United States Patent
McDaniel et al.

(10) Patent No.: US 10,655,056 B2
(45) Date of Patent: *May 19, 2020

(54) GUANIDINE- OR GUANIDINIUM-CONTAINING COMPOUNDS FOR TREATMENT OF SUBTERRANEAN FORMATIONS

(71) Applicant: Halliburton Energy Services, Inc., Houston, TX (US)

(72) Inventors: Cato Russell McDaniel, The Woodlands, TX (US); William Walter Shumway, Spring, TX (US); Eric Davidson, Aberdeen (GB)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/372,130

(22) Filed: Apr. 1, 2019

(65) Prior Publication Data

US 2019/0225873 A1 Jul. 25, 2019

Related U.S. Application Data

(63) Continuation of application No. 15/313,479, filed as application No. PCT/US2014/049090 on Jul. 31, 2014, now Pat. No. 10,294,410.

(51) Int. Cl.
*C09K 8/575* (2006.01)
*C09K 8/64* (2006.01)
(Continued)

(52) U.S. Cl.
CPC .............. *C09K 8/64* (2013.01); *C07C 279/14* (2013.01); *C07D 487/04* (2013.01); *C08G 69/10* (2013.01);
(Continued)

(58) Field of Classification Search
None
See application file for complete search history.

(56) References Cited

U.S. PATENT DOCUMENTS

| 4,605,068 A | 8/1986 | Young et al. |
| 4,664,818 A | 5/1987 | Halliday et al. |

(Continued)

FOREIGN PATENT DOCUMENTS

| WO | 99/09109 | 2/1999 |
| WO | 2006013595 | 2/2006 |

(Continued)

OTHER PUBLICATIONS

ISRWO International Search Report and Written Opinion for PCT/US2014/049090 dated May 12, 2015.
(Continued)

*Primary Examiner* — Andrew Sue-Ako
(74) *Attorney, Agent, or Firm* — Tenley Krueger; C. Tumey Law Group PLLC

(57) ABSTRACT

Various embodiments disclosed relate to guanidine- or guanidinium-containing clay or shale stabilizers for treatment of subterranean formations. In various embodiments, the present invention provides a method of treating a subterranean formation that can include placing a composition including a clay or shale stabilizer including at least one of a substituted guanidine group and a substituted guanidinium group in a subterranean formation.

18 Claims, 2 Drawing Sheets

(51) Int. Cl.

| | |
|---|---|
| *C09K 8/42* | (2006.01) |
| *C09K 8/60* | (2006.01) |
| *C09K 8/035* | (2006.01) |
| *C07C 279/14* | (2006.01) |
| *C07D 487/04* | (2006.01) |
| *C08G 69/10* | (2006.01) |
| *C09K 8/04* | (2006.01) |
| *C09K 8/32* | (2006.01) |
| *C09K 8/36* | (2006.01) |
| *C09K 8/68* | (2006.01) |
| *C09K 8/80* | (2006.01) |
| *E21B 21/00* | (2006.01) |
| *E21B 33/13* | (2006.01) |
| *E21B 43/26* | (2006.01) |
| *C09K 8/52* | (2006.01) |
| *C09K 8/62* | (2006.01) |
| *C09K 8/74* | (2006.01) |

(52) U.S. Cl.
CPC .............. *C09K 8/035* (2013.01); *C09K 8/04* (2013.01); *C09K 8/32* (2013.01); *C09K 8/36* (2013.01); *C09K 8/42* (2013.01); *C09K 8/607* (2013.01); *C09K 8/68* (2013.01); *C09K 8/80* (2013.01); *C09K 8/805* (2013.01); *E21B 21/00* (2013.01); *E21B 33/13* (2013.01); *E21B 43/26* (2013.01); *C09K 8/52* (2013.01); *C09K 8/62* (2013.01); *C09K 8/74* (2013.01); *C09K 2208/02* (2013.01); *C09K 2208/12* (2013.01)

(56) References Cited

U.S. PATENT DOCUMENTS

| | | |
|---|---|---|
| 4,666,613 A | 5/1987 | Schapira et al. |
| 4,719,021 A | 1/1988 | Branch, III |
| 4,725,362 A | 2/1988 | Dugat |
| 5,197,544 A | 3/1993 | Himes |
| 5,380,706 A | 1/1995 | Himes et al. |
| 5,424,284 A | 1/1995 | Patel et al. |
| 5,635,458 A | 6/1997 | Lee et al. |
| 5,728,653 A | 3/1998 | Audibert et al. |
| 5,771,971 A | 6/1998 | Horton et al. |
| 5,908,814 A | 6/1999 | Patel et al. |
| 6,247,543 B1 | 6/2001 | Patel et al. |
| 6,281,172 B1 | 8/2001 | Warren et al. |
| 6,426,321 B1 | 7/2002 | Durrieu et al. |
| 6,484,821 B1 | 11/2002 | Patel et al. |
| 6,544,933 B1 | 4/2003 | Reid et al. |
| 6,609,578 B2 | 8/2003 | Patel et al. |
| 7,091,159 B2 | 8/2006 | Eoff et al. |
| 7,992,654 B2 | 8/2011 | De Boer |
| 8,122,975 B2 | 2/2012 | Belcher et al. |
| 8,211,835 B2 | 7/2012 | Howard et al. |
| 8,631,868 B1 | 1/2014 | Murphy et al. |
| 10,294,410 B2 * | 5/2019 | McDaniel .............. C09K 8/035 |
| 2002/0155956 A1 | 10/2002 | Chamberlain et al. |
| 2003/0106718 A1 | 6/2003 | Patel et al. |
| 2006/0116296 A1 | 6/2006 | Kippie et al. |
| 2010/0137168 A1 | 6/2010 | Quintero et al. |
| 2011/0114387 A1 | 5/2011 | Belcher et al. |
| 2011/0290482 A1 | 12/2011 | Weerasooriya et al. |
| 2012/0015852 A1 | 1/2012 | Quintero et al. |
| 2012/0067585 A1 | 3/2012 | Murphy et al. |
| 2012/0298357 A1 | 11/2012 | Ezell et al. |
| 2014/0290955 A1 * | 10/2014 | Chen ..................... C09K 8/528 166/305.1 |

FOREIGN PATENT DOCUMENTS

| | | |
|---|---|---|
| WO | 2006013597 | 2/2006 |
| WO | 2012176000 | 12/2012 |

OTHER PUBLICATIONS

Final Office Action for U.S. Appl. No. 15/313,479 dated Apr. 30, 2018.
Notice of Allowance for U.S. Appl. No. 15/313,479 dated Jan. 2, 2019.
Office Action for U.S. Appl. No. 15/313,479 dated Apr. 14, 2017.
Office Action for U.S. Appl. No. 15/313,479 dated Aug. 16, 2018.
Australian Examination Report for Application No. 2014402368 dated Feb. 23, 2018.
Khaled et al., "Chemical and Electrochemical Investigation of L-Arginine as Corrosion Inhibitor for Steel in Hydrochloric Acid Solutions", Int. J. Electrochem. Sci., 2013 vol. 8, pp. 1409-1421.
Clayseal® Plus product sheet, Halliburton Energy Services, Inc., Mar. 25, 2010.
Kla-Cure product sheet, Mi Swaco, 2008.
Canadian Office Action for Application No. 2,951,241, dated May 24, 2019.

* cited by examiner

(12) United States Patent
US 10,655,056 B2

GUANIDINE- OR GUANIDINIUM-CONTAINING COMPOUNDS FOR TREATMENT OF SUBTERRANEAN FORMATIONS

BACKGROUND

Swelling clays can be a major mechanism of formation damage due to loss of mobility of hydrocarbon fluids in the formation. When clays encounter foreign water, they can swell, causing a loss of permeability. The swelling can cause portions of the clay and adjacent fines to become mobile within the production stream and, too frequently, encounter constrictions in capillaries, where they can bridge off the capillaries and severely diminish the flow rate of hydrocarbons to the wellbore. Sometimes the loss of permeability observed is due to clay swelling without migration, but often clay swelling is accompanied by migration of clay and other fines. Non-swelling clays may also respond to the foreign water and begin to migrate.

Shale is a fine-grained, fissile, detrital sedimentary rock formed by consolidation of clay- and silt-sized particles into thin, relatively impermeable layers. Some shales encountered during subterranean operations can be sensitive to water, due in part to clay content and the ionic composition of the clay. Such shales, also known as heaving or sloughing shales, can have a tendency to degrade, such as swell or crack, upon contact with various downhole fluids, such as drilling fluids and fracturing fluids. The complications associated with shale degradation during drilling may substantially increase the time and cost of drilling. The degradation of shales in a borehole can render the borehole walls unstable. The heaving shale material can slough and cave into the borehole. Degradation of the shale can interrupt circulation of the drilling fluid and cause greater friction between the drill string and the wellbore. Sloughing of shale material into the borehole can cause the drill stem to become stuck and can enlarge the borehole, with the result that large subterranean cavities are formed. The degradation of the shale may interfere with attempts to maintain the integrity of drilled cuttings traveling up the well bore until such time as the cuttings can be removed by solids control equipment located at the surface. Degradation of drilled cuttings prior to their removal at the surface may prolong drilling time because shale particles traveling up the well bore can break up into smaller and smaller particles, which can expose new surface area of the shale particles to the drilling fluid and lead to further absorption of water and degradation. Where sloughing occurs while the drilling bit is being changed at the surface, the borehole fills up and must be cleared before drilling can proceed. The heaving shale material taken up into the drilling fluid can adversely affect the viscosity characteristics of the drilling fluid to the point where the fluid must be chemically treated to reduce the viscosity thereof or it must be diluted followed by the addition of weighing material to maintain a given mud weight.

Using oil-based fluids instead of aqueous-based fluids is one method of inhibiting clay swelling and shale degradation. However, oil-based fluids are often environmentally undesirable because they may be toxic. Accordingly, environmental regulations enacted by numerous countries have curtailed the use of oil-based fluids. Another method is to use clay or shale stabilizers. However, many clay or shale stabilizers are expensive and are environmentally undesirable due to toxicity or lack of biodegradability, and can cause damage to subterranean formations.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
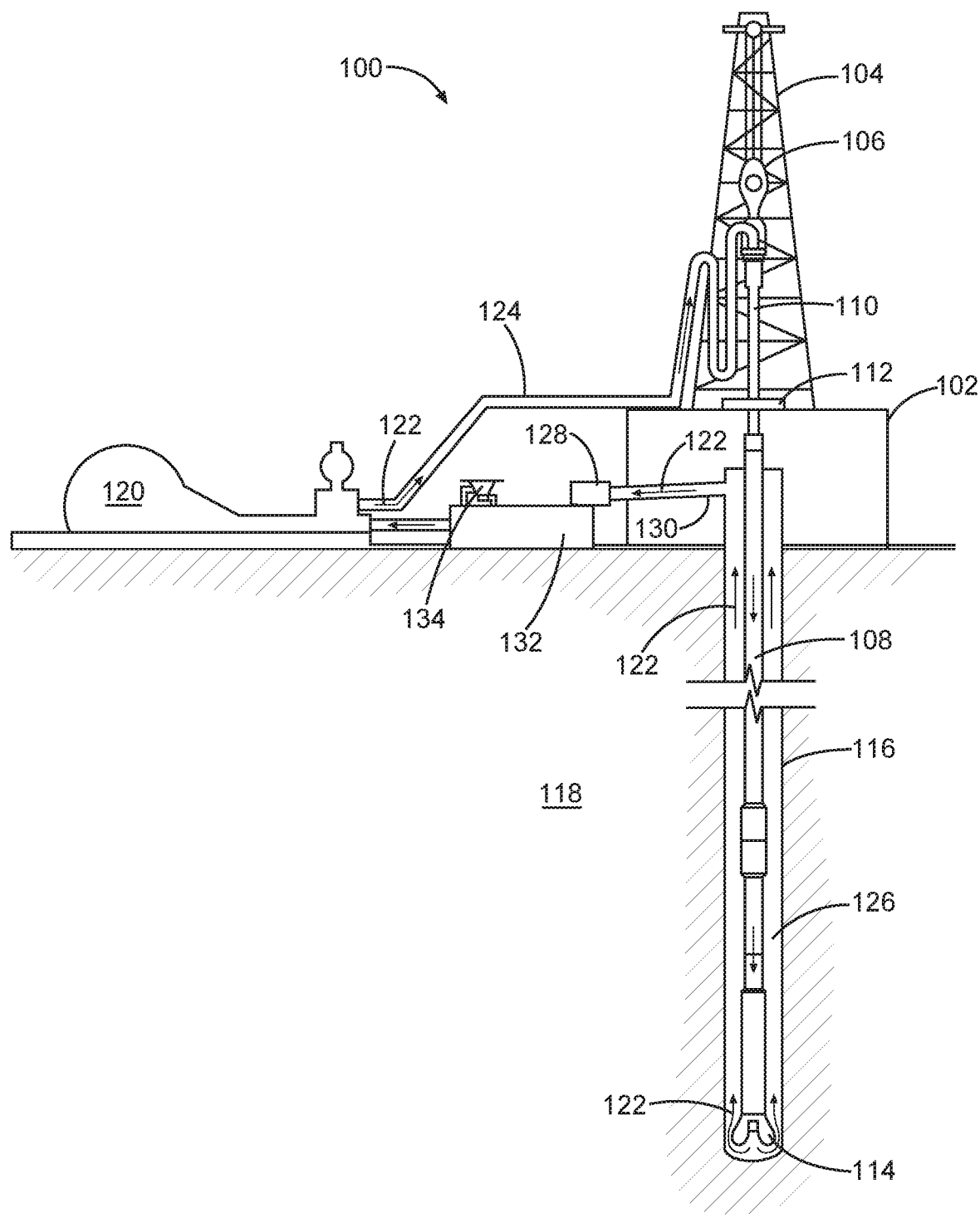
FIG. 1 illustrates a drilling assembly, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Selected substituents within the compounds described herein are present to a recursive degree. In this context, "recursive substituent" means that a substituent may recite another instance of itself or of another substituent that itself recites the first substituent. Recursive substituents are an intended aspect of the disclosed subject matter. Because of the recursive nature of such substituents, theoretically, a large number may be present in any given claim. One of ordinary skill in the art of organic chemistry understands that the total number of such substituents is reasonably limited by the desired properties of the compound intended. Such properties include, by way of example and not limitation, physical properties such as molecular weight, solubility, and practical properties such as ease of synthesis. Recursive substituents can call back on themselves any suitable number of times, such as about 1 time, about 2 times, 3, 4, 5, 6, 7, 8, 9, 10, 15, 20, 30, 50, 100, 200, 300, 400, 500, 750, 1000, 1500, 2000, 3000, 4000, 5000, 10,000, 15,000, 20,000, 30,000, 50,000, 100,000, 200,000, 500,000, 750,000, or about 1,000,000 times or more.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen (in examples that include other carbon atoms) or a carbon-based moiety, and wherein the carbon-based moiety can itself be further substituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted with J; or wherein two R groups bonded to a nitrogen atom or to adjacent nitrogen atoms can together with the nitrogen atom or atoms form a heterocyclyl, which can be mono- or independently multi-substituted with J.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof.

The term "solvent" as used herein refers to a liquid that can dissolve a solid, liquid, or gas. Nonlimiting examples of solvents are silicones, organic compounds, water, alcohols, ionic liquids, and supercritical fluids.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species i having $n_i$ molecules of molecular weight $M_i$ through the formula $M_n = \Sigma M_i n_i / \Sigma n_i$. The number-average molecular weight can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

The term "room temperature" as used herein refers to a temperature of about 15° C. to 28° C.

The term "standard temperature and pressure" as used herein refers to 20° C. and 101 kPa.

As used herein, "degree of polymerization" is the number of repeating units in a polymer.

As used herein, the term "polymer" refers to a molecule having at least one repeating unit and can include copolymers.

The term "copolymer" as used herein refers to a polymer that includes at least two different repeating units. A copolymer can include any suitable number of repeating units.

The term "downhole" as used herein refers to under the surface of the earth, such as a location within or fluidly connected to a wellbore.

As used herein, the term "drilling fluid" refers to fluids, slurries, or muds used in drilling operations downhole, such as during the formation of the wellbore.

As used herein, the term "stimulation fluid" refers to fluids or slurries used downhole during stimulation activities of the well that can increase the production of a well, including perforation activities. In some examples, a stimulation fluid can include a fracturing fluid or an acidizing fluid.

As used herein, the term "clean-up fluid" refers to fluids or slurries used downhole during clean-up activities of the well, such as any treatment to remove material obstructing the flow of desired material from the subterranean formation. In one example, a clean-up fluid can be an acidification treatment to remove material formed by one or more perforation treatments. In another example, a clean-up fluid can be used to remove a filter cake.

As used herein, the term "fracturing fluid" refers to fluids or slurries used downhole during fracturing operations.

As used herein, the term "spotting fluid" refers to fluids or slurries used downhole during spotting operations, and can be any fluid designed for localized treatment of a downhole region. In one example, a spotting fluid can include a lost circulation material for treatment of a specific section of the wellbore, such as to seal off fractures in the wellbore and prevent sag. In another example, a spotting fluid can include a water control material. In some examples, a spotting fluid can be designed to free a stuck piece of drilling or extraction equipment, can reduce torque and drag with drilling lubricants, prevent differential sticking, promote wellbore stability, and can help to control mud weight.

As used herein, the term "completion fluid" refers to fluids or slurries used downhole during the completion phase of a well, including cementing compositions.

As used herein, the term "remedial treatment fluid" refers to fluids or slurries used downhole for remedial treatment of a well. Remedial treatments can include treatments designed to increase or maintain the production rate of a well, such as stimulation or clean-up treatments.

As used herein, the term "abandonment fluid" refers to fluids or slurries used downhole during or preceding the abandonment phase of a well.

As used herein, the term "acidizing fluid" refers to fluids or slurries used downhole during acidizing treatments. In one example, an acidizing fluid is used in a clean-up operation to remove material obstructing the flow of desired material, such as material formed during a perforation operation. In some examples, an acidizing fluid can be used for damage removal.

As used herein, the term "cementing fluid" refers to fluids or slurries used during cementing operations of a well. For example, a cementing fluid can include an aqueous mixture including at least one of cement and cement kiln dust. In another example, a cementing fluid can include a curable resinous material such as a polymer that is in an at least partially uncured state.

As used herein, the term "water control material" refers to a solid or liquid material that interacts with aqueous material downhole, such that hydrophobic material can more easily travel to the surface and such that hydrophilic material (including water) can less easily travel to the surface. A water control material can be used to treat a well to cause the proportion of water produced to decrease and to cause the proportion of hydrocarbons produced to increase, such as by selectively binding together material between water-producing subterranean formations and the wellbore while still allowing hydrocarbon-producing formations to maintain output.

As used herein, the term "packer fluid" refers to fluids or slurries that can be placed in the annular region of a well between tubing and outer casing above a packer. In various examples, the packer fluid can provide hydrostatic pressure in order to lower differential pressure across the sealing element, lower differential pressure on the wellbore and casing to prevent collapse, and protect metals and elastomers from corrosion.

As used herein, the term "fluid" refers to liquids and gels, unless otherwise indicated.

As used herein, the term "subterranean material" or "subterranean formation" refers to any material under the surface of the earth, including under the surface of the bottom of the ocean. For example, a subterranean formation or material can be any section of a wellbore and any section of a subterranean petroleum- or water-producing formation or region in fluid contact with the wellbore. Placing a material in a subterranean formation can include contacting the material with any section of a wellbore or with any subterranean region in fluid contact therewith. Subterranean materials can include any materials placed into the wellbore such as cement, drill shafts, liners, tubing, or screens; placing a material in a subterranean formation can include contacting with such subterranean materials. In some examples, a subterranean formation or material can be any below-ground region that can produce liquid or gaseous petroleum materials, water, or any section below-ground in fluid contact therewith. For example, a subterranean formation or material can be at least one of an area desired to be fractured, a fracture or an area surrounding a fracture, and a flow pathway or an area surrounding a flow pathway, wherein a fracture or a flow pathway can be optionally fluidly connected to a subterranean petroleum- or water-producing region, directly or through one or more fractures or flow pathways.

As used herein, "treatment of a subterranean formation" can include any activity directed to extraction of water or petroleum materials from a subterranean petroleum- or water-producing formation or region, for example, including drilling, stimulation, hydraulic fracturing, clean-up, acidizing, completion, cementing, remedial treatment, abandonment, and the like.

As used herein, a "flow pathway" downhole can include any suitable subterranean flow pathway through which two subterranean locations are in fluid connection. The flow pathway can be sufficient for petroleum or water to flow from one subterranean location to the wellbore or vice-versa. A flow pathway can include at least one of a hydraulic fracture, and a fluid connection across a screen, across gravel pack, across proppant, including across resin-bonded proppant or proppant deposited in a fracture, and across sand. A flow pathway can include a natural subterranean passageway through which fluids can flow. In some embodiments, a flow pathway can be a water source and can include water. In some embodiments, a flow pathway can be a petroleum source and can include petroleum. In some embodiments, a flow pathway can be sufficient to divert from a wellbore, fracture, or flow pathway connected thereto at least one of water, a downhole fluid, or a produced hydrocarbon.

As used herein, a "carrier fluid" refers to any suitable fluid for suspending, dissolving, mixing, or emulsifying with one or more materials to form a composition. For example, the carrier fluid can be at least one of crude oil, dipropylene glycol methyl ether, dipropylene glycol dimethyl ether, dipropylene glycol methyl ether, dipropylene glycol dimethyl ether, dimethyl formamide, diethylene glycol methyl ether, ethylene glycol butyl ether, diethylene glycol butyl ether, butylglycidyl ether, propylene carbonate, D-limonene, a $C_2$-$C_{40}$ fatty acid $C_1$-$C_{10}$ alkyl ester (e.g., a fatty acid methyl ester), tetrahydrofurfuryl methacrylate, tetrahydrofurfuryl acrylate, 2-butoxy ethanol, butyl acetate, butyl lactate, furfuryl acetate, dimethyl sulfoxide, dimethyl formamide, a petroleum distillation product of fraction (e.g., diesel, kerosene, napthas, and the like) mineral oil, a hydrocarbon oil, a hydrocarbon including an aromatic carbon-carbon bond (e.g., benzene, toluene), a hydrocarbon including an alpha olefin, xylenes, an ionic liquid, methyl ethyl ketone, an ester of oxalic, maleic or succinic acid, methanol, ethanol, propanol (iso- or normal-), butyl alcohol (iso-, tert-, or normal-), an aliphatic hydrocarbon (e.g., cyclohexanone, hexane), water, brine, produced water, flowback water, brackish water, and sea water. The fluid can form about 0.001 wt % to about 99.999 wt % of a composition, or a mixture including the same, or about 0.001 wt % or less, 0.01 wt %, 0.1, 1, 2, 3, 4, 5, 6, 8, 10, 15, 20, 25, 30, 35, 40, 45, 50, 55, 60, 65, 70, 75, 80, 85, 90, 95, 96, 97, 98, 99, 99.9, 99.99, or about 99.999 wt % or more.

As used herein, a "shale stabilizer" is a material that slows or prevents the mechanical or chemical disaggregation of shale.

As used herein, a "clay stabilizer" is a material that slows or prevents the mechanical or chemical disaggregation of clay.

The polymers described herein can terminate in any suitable way. In some embodiments, the polymers can terminate with an end group that is independently chosen from a suitable polymerization initiator, —H, —OH, a substituted or unsubstituted ($C_1$-$C_{20}$)hydrocarbyl (e.g., ($C_1$-$C_{10}$)alkyl or ($C_6$-$C_{20}$)aryl) at least one of interrupted with 0, 1, 2, or 3 groups independently substituted from —O—, substituted or unsubstituted —NH—, and —S—, a poly (substituted or unsubstituted ($C_1$-$C_{20}$)hydrocarbyloxy), and a poly(substituted or unsubstituted ($C_1$-$C_{20}$)hydrocarbylamino).

In various embodiments, the present invention provides a method of treating a subterranean formation. The method includes placing a composition including a clay or shale stabilizer in a subterranean formation. The clay stabilizer or shale stabilizer includes at least one of a substituted guanidine group and a substituted guanidinium group.

In various embodiments, the present invention provides a method of treating a subterranean formation. The method includes placing a drilling fluid, fracturing fluid, cementing fluid, completion fluid, logging fluid, spotting fluid, or a packer fluid in a subterranean formation. The drilling fluid, fracturing fluid, cementing fluid, completion fluid, logging fluid, spotting fluid, or packer fluid includes a clay or shale stabilizer having the following structure

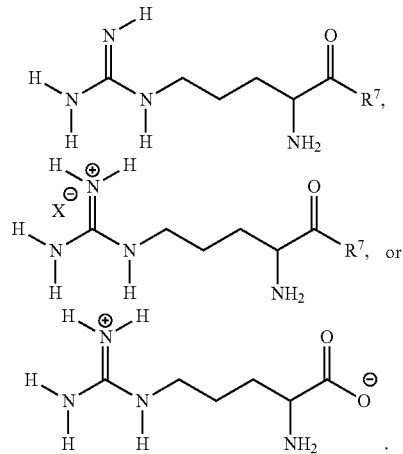

The variable $R^7$ is selected from the group consisting of —OH, —$OR^8$, —[$O^-$]$Y^+$, and —$O^-$. The variable $R^8$ is a ($C_1$-$C_{50}$)hydrocarbyl. The variable $Y^+$ is a counterion. The clay or shale stabilizer is about 0.001 wt % to about 10 wt % of the drilling fluid, fracturing fluid, cementing fluid, completion fluid, logging fluid, spotting fluid, or the packer fluid.

In various embodiments, the present invention provides a method of treating a subterranean formation. The method includes placing a composition including a clay or shale stabilizer in a subterranean formation. The clay or shale stabilizer includes at least one of an unsubstituted guanidine and an unsubstituted guanidinium. The guanidine and guanidinium are free of complexation with polyvalent metals.

In various embodiments, the present invention provides a system including a composition including a clay or shale stabilizer including at least one of a substituted guanidine group and a substituted guanidinium group. The system also includes a subterranean formation including the composition therein.

In various embodiments, the present invention provides a composition for treatment of a subterranean formation. The composition includes a clay or shale stabilizer including at least one of a substituted guanidine group and a substituted guanidinium group.

In various embodiments, the present invention provides a drilling fluid, fracturing fluid, cementing fluid, completion fluid, logging fluid, spotting fluid, or a packer fluid for treatment of a subterranean formation. The composition includes a clay or shale stabilizer having the following structure

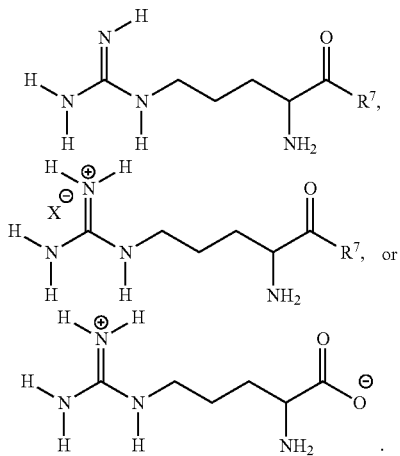

The variable $R^7$ is selected from the group consisting of —OH, —OR$^8$, —[O$^-$]Y$^+$, and —O$^-$. The variable $R^8$ is a ($C_1$-$C_{50}$)hydrocarbyl. The variable Y$^+$ is a counterion. The clay or shale stabilizer is about 0.001 wt % to about 10 wt % of the drilling fluid, fracturing fluid, cementing fluid, completion fluid, logging fluid, spotting fluid, or the packer fluid.

In various embodiments, the present invention provides a method of preparing a composition for treatment of a subterranean formation. The method includes forming a composition including a clay or shale stabilizer including at least one of a substituted guanidine group and a substituted guanidinium group.

Various embodiments of the present invention provide certain advantages over other methods, composition, and systems for stabilization of clay or shale. For example, in some embodiments, unlike other clay or shale inhibitors, the clay or shale stabilizer can be naturally derived, such as from arginine, a common amino acid. In some embodiments, unlike other clay or shale inhibitors, the clay or shale stabilizer can be readily biodegradable. In some embodiments, the clay or shale stabilizer can have less or no toxicity as compared to other clay or shale inhibitors. In various embodiments, the clay or shale stabilizer can stabilize or inhibit clay or shale disaggregation more effectively than other clay or shale inhibitors. In various embodiments, the amount of clay or shale stabilizer needed can be less costly to effect a given amount of stabilization of clay or shale than the amount of another clay or shale inhibitor needed to effect the same amount of stabilization.

Method of Treatment of a Subterranean Formation.

In some embodiments, the present invention provides a method of treating a subterranean formation. The method includes placing a composition including a clay or shale stabilizer including at least one of a substituted guanidine group and a substituted guanidinium group in a subterranean formation. The composition can include a clay stabilizer that is not a shale stabilizer, a shale stabilizer that is not a clay stabilizer, or a stabilizer that is both a clay stabilizer and a shale stabilizer. The composition can include one or more clay stabilizers or shale stabilizers having at least one of a substituted guanidine group and a substituted guanidinium group. The method can include obtaining or providing the composition. The obtaining or providing of the composition can occur at any suitable time and at any suitable location. The obtaining or providing of the composition can occur above the surface. The obtaining or providing of the composition can occur in the subterranean formation (e.g., downhole). The placing of the composition in the subterranean formation can include contacting the composition and any suitable part of the subterranean formation, or contacting the composition and a subterranean material, such as any suitable subterranean material. The subterranean formation can be any suitable subterranean formation.

In some examples, the placing of the composition in the subterranean formation includes contacting the composition with or placing the composition in at least one of a fracture, at least a part of an area surrounding a fracture, a flow pathway, an area surrounding a flow pathway, and an area desired to be fractured. The placing of the composition in the subterranean formation can be any suitable placing and can include any suitable contacting between the subterranean formation and the composition. The placing of the composition in the subterranean formation can include using the composition as a drilling fluid or as a cementing fluid.

The method can include hydraulic fracturing, such as a method of hydraulic fracturing to generate a fracture or flow pathway. The placing of the composition in the subterranean formation or the contacting of the subterranean formation and the hydraulic fracturing can occur at any time with respect to one another; for example, the hydraulic fracturing can occur at least one of before, during, and after the contacting or placing. In some embodiments, the contacting or placing occurs during the hydraulic fracturing, such as during any suitable stage of the hydraulic fracturing, such as during at least one of a pre-pad stage (e.g., during injection of water with no proppant, and additionally optionally mid- to low-strength acid), a pad stage (e.g., during injection of fluid only with no proppant, with some viscosifier, such as to begin to break into an area and initiate fractures to produce sufficient penetration and width to allow proppant-laden later stages to enter), or a slurry stage of the fracturing (e.g., viscous fluid with proppant). The method can include performing a stimulation treatment at least one of before, during, and after placing the composition in the subterranean formation in the fracture, flow pathway, or area surrounding the same. The stimulation treatment can be, for example, at least one of perforating, acidizing, injecting of cleaning fluids, propellant stimulation, and hydraulic fracturing. In some embodiments, the stimulation treatment at least partially generates a fracture or flow pathway where the composition is placed or contacted, or the composition is placed or contacted to an area surrounding the generated fracture or flow pathway.

In some embodiments, the method can be a method of drilling, stimulation, fracturing, spotting, clean-up, completion, remedial treatment, applying a pill, acidizing, cementing, or a combination thereof, wherein the composition can be or can include a drilling fluid, stimulation fluid, a fracturing fluid, a spotting fluid, a clean-up fluid, a completion fluid, a remedial treatment fluid, a pill, an acidization fluid, a cementing fluid, respectively.

In some embodiments, the composition can include carrier fluid. The carrier fluid can be any suitable fluid or combination of fluids, such as an aqueous fluid, an organic fluid, or an oil. The carrier fluid can be any suitable proportion of the composition, such as about 0.000.1 wt % to 99.999.9 wt % of the composition, or about 0.01 wt % to about 99.99 wt %, about 0.1 wt % to about 99.9 wt %, or about 20 wt % to about 90 wt %, about 50 wt % to about 99.999 wt %, or about 0.000.1 wt % or less, or about 0.001 wt %, 0.01, 0.1, 1, 2, 3, 4, 5, 10, 15, 20, 30, 40, 50, 60, 70, 80, 85, 90, 91, 92, 93, 94, 95, 96, 97, 98, 99, 99.9, 99.99, 99.999 wt %, or about 99.999.9 wt % or more of the composition can be the carrier fluid.

In some embodiments, the composition can include an aqueous liquid. The aqueous liquid can be any suitable aqueous liquid, such as at least one of water, brine, produced water, flowback water, brackish water, and sea water. In some embodiments, the aqueous liquid can include at least one of an aqueous drilling fluid, aqueous fracturing fluid, aqueous diverting fluid, and an aqueous fluid loss control fluid. In some embodiments, the aqueous liquid can be the aqueous phase of an emulsion (e.g., the composition can include an emulsion having as the aqueous phase the aqueous liquid). The aqueous liquid can be any suitable proportion of the composition, such that the composition can be used as described herein. For example, about 0.000.1 wt % to 99.999.9 wt % of the composition can be the aqueous liquid, or about 0.01 wt % to about 99.99 wt %, about 0.1 wt % to about 99.9 wt %, or about 20 wt % to about 90 wt %, or about 0.000.1 wt % or less, or about 0.001 wt %, 0.01, 0.1, 1, 2, 3, 4, 5, 10, 15, 20, 30, 40, 50, 60, 70, 80, 85, 90, 91, 92, 93, 94, 95, 96, 97, 98, 99, 99.9, 99.99, 99.999 wt %, or about 99.999.9 wt % or more of the composition can be the aqueous liquid.

The aqueous liquid can be a salt water. The salt can be any suitable salt, such as at least one of NaBr, $CaCl_2$, $CaBr_2$, $ZnBr_2$, KCl, NaCl, a magnesium salt, a bromide salt, a formate salt, an acetate salt, and a nitrate salt. The aqueous liquid can have any suitable total dissolved solids level (e.g., wherein the dissolved solids correspond to dissolved salts), such as about 1,000 mg/L to about 250,000 mg/L, or about 1,000 mg/L or less, or about 5,000 mg/L, 10,000, 15,000, 20,000, 25,000, 30,000, 40,000, 50,000, 75,000, 100,000, 125,000, 150,000, 175,000, 200,000, 225,000, or about 250,000 mg/L or more. The aqueous liquid can have any suitable salt concentration, such as about 1,000 ppm to about 300,000 ppm, or about 1,000 ppm to about 150,000 ppm, or about 1,000 ppm or less, or about 5,000 ppm, 10,000, 15,000, 20,000, 25,000, 30,000, 40,000, 50,000, 75,000, 100,000, 125,000, 150,000, 175,000, 200,000, 225,000, 250,000, 275,000, or about 300,000 ppm or more. In some examples, the aqueous liquid can have a concentration of at least one of NaBr, $CaCl_2$, $CaBr_2$, $ZnBr_2$, KCl, and NaCl of about 0.1% w/v to about 20% w/v, or about 0.1% w/v or less, or about 0.5% w/v, 1, 2, 3, 4, 5, 6, 7, 8, 9, 10, 11, 12, 13, 14, 15, 16, 17, 18, 19, 20, 21, 22, 23, 24, 25, 26, 27, 28, 29, or about 30% w/v or more.

The composition can be oil-based (e.g., over 50 wt % oil or organic fluids) or water-based (e.g., over 50 wt % aqueous fluids). In some embodiments, the composition can be an emulsion. The emulsion can be an aqueous-external emulsion or an oil-external emulsion. The clay or shale stabilizer can be at least partially dissolved in the water-phase of an emulsion, at least partially dissolved in an oil-phase of an emulsion, or a combination thereof.

Clay or Shale Stabilizer.

The composition can include one clay or shale stabilizer, or more than one clay or shale stabilizer. The stabilizer can be a clay stabilizer, a shale stabilizer, or a clay and shale stabilizer. Any suitable proportion of the composition can be the clay or shale stabilizer, such as about 0.000.1 wt % to 99.999.9 wt % of the composition, or about 0.01 wt % to about 99.99 wt %, about 0.001 wt % to about 99.9 wt %, or about 0.001 wt % to about 10 wt %, or about 0.000.1 wt % or less, or about 0.000,001 wt %, 0.000,1, 0.001, 0.01, 0.1, 1, 2, 3, 4, 5, 6, 7, 8, 9, 10, 15, 20, 30, 40, 50, 60, 70, 80, 85, 90, 91, 92, 93, 94, 95, 96, 97, 98, 99, 99.9, 99.99, 99.999 wt %, or about 99.999.9 wt % or more of the composition. In some embodiments, the clay or shale stabilizer can be or can be derivable from arginine, such as L-arginine, such as via at least one reaction selected from alkoxylation, alkalyation, alkylcarboxylation, alkylesterification, halogenation, oxidation, and amidification. In various embodiments, the solubility of the clay or shale stabilizer can be tuned, such as by using long-chain esters or substituents to enhance oil or organic solubility, or by using acids, salts, or guanidinium groups to enhance water solubility. In various embodiments, the clay or shale stabilizer can operate in any suitable way, such as by substituting for other ions in a clay lattice which make it more prone to swelling.

In some embodiments, the clay or shale stabilizer can be an unsubstituted guanidine or guanidinium having the structure:

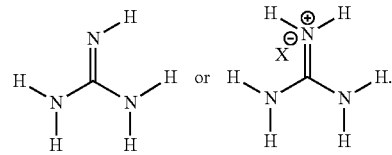

The variable $X^-$ is counterion. The guanidine and guanidinium can be free of complexation with polyvalent metals. Complexation can be at least one interaction with the metal chosen from at least one of ionic, covalent, dipole-dipole, London dispersion force, and hydrogen bonding, wherein the interaction is of sufficient strength that a stable complex between the guanidine or guanidinium and the metal is formed. In some embodiments, the guanidine and guanidinium are free of complexation with metals, such as aluminum. In some embodiments, the guanidine and guanidinium are free of complexation with aluminum hydroxide, sodium aluminate, aluminum sulfate, and aluminum phosphate.

In some embodiments, the clay or shale stabilizer can be a compound that includes a substituted guanidine group or a substituted guanidinium group. The stabilizer can include one or more substituted guanidine groups, one or more substituted guanidinium groups, or a combination thereof. In some embodiments, the clay or shale stabilizer has the structure:

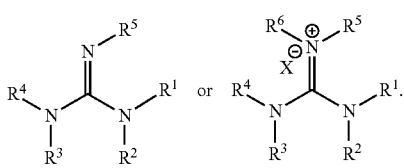

The variables $R^1$, $R^2$, $R^3$, $R^4$, $R^5$, and $R^6$ can each be independently selected from —H, halogen, an organic group, and substituted or unsubstituted $(C_1-C_{30})$hydrocarbyl interrupted by 0, 1, 2, or 3 of at least one of —O—, —S—, and substituted or unsubstituted —NH—, or at least one pair of $R^1$, $R^2$, $R^3$, $R^4$, $R^5$, and $R^6$ can together form a substituted or unsubstituted $(C_2-C_{20})$hydrocarbylene such that at least two of the nitrogen atoms in the clay or shale stabilizer are part of a heterocycle including the substituted or unsubstituted $(C_2-C_{20})$hydrocarbylene. Optionally, at least one of $R^1$, $R^2$, $R^3$, $R^4$, $R^5$, and $R^6$ can be bonded to at least one $R^1$, $R^2$, $R^3$, $R^4$, $R^5$, and $R^6$ on a different guanidine or guanidinium group in the same clay or shale stabilizer. The guanidine or guanidinium is substituted, such that at least one of $R^1$, $R^2$, $R^3$, $R^4$, and $R^5$ is not —H. The variable $X^-$ is a counterion. In some examples, the variable $R^6$ can be —H. A guanidine group can distribute charge between the nitrogen atoms, and can thus be represented by the resonance structures:

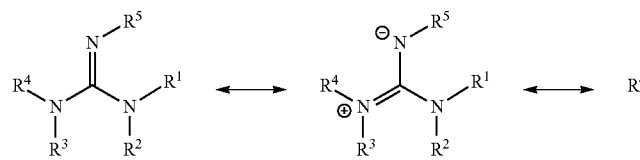 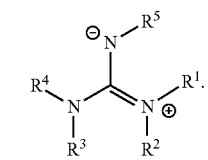

A guanidinium group can distribute charge between the nitrogen atoms, and can thus be represented by the resonance structures:

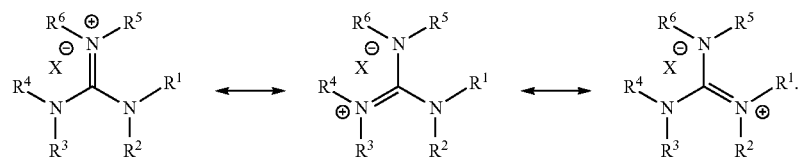 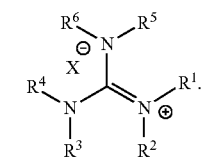

The variable $X^-$ can be any suitable anionic counterion. The variable $X^-$ can be selected from the group consisting of fluoride, chloride, iodide, bromide, nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate, acetate, formate, oxide, sulfide, nitride, arsenate, phosphate, arsenite, hydrogen phosphate, sulfate, thiosulfate, sulfite, carbonate, chromate, dichromate, peroxide, and oxalate.

The variables $R^2$, $R^3$, $R^4$, $R^5$, and $R^6$ can each be independently selected from —H and substituted or unsubstituted $(C_1-C_{15})$alkyl. The variables $R^2$, $R^3$, $R^4$, $R^5$, and $R^6$ can be each independently selected from —H and substituted or unsubstituted $(C_1-C_5)$alkyl. The variables $R^2$, $R^3$, $R^4$, $R^5$, and $R^6$ can each be —H.

In some embodiments, at least one pair of $R^1$, $R^2$, $R^3$, $R^4$, $R^5$, and $R^6$ can together form a $(C_2-C_5)$alkylene such that at least two of the nitrogen atoms in the clay or shale stabilizer are part of a heterocycle including the $(C_2-C_5)$alkylene. At least one pair of $R^1$, $R^2$, $R^3$, $R^4$, $R^5$, and $R^6$ together form a $(C_3)$alkylene such that at least two of the nitrogen atoms in the clay or shale stabilizer are part of a heterocycle including the $(C_3)$alkylene. In some embodiments, the clay or shale stabilizer is 1,5,7-triazabicyclo[4.4.0]dec-5-ene, having the structure:

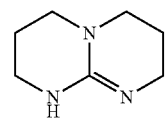

The clay or shale stabilizer can be a polymer, such as a polymer having the substituted guanidine group or substituted guanidinium group as pendant groups on the backbone of the polymer. The polymer can have any suitable degree of polymerization, and can include any suitable proportion of repeating groups that include a pendant guanidine or guanidinium group. In some embodiments of a polymeric clay or shale stabilizer, at least one of $R^1$, $R^2$, $R^3$, $R^4$, $R^5$, and $R^6$ can be bonded to at least one $R^1$, $R^2$, $R^3$, $R^4$, $R^5$, and $R^6$ on a different guanidine or guanidinium group in the same clay or shale stabilizer.

In some embodiments, the clay or shale stabilizer includes two or more of the guanidine or guanidinium groups connected to one another via a $(C_1-C_{30})$hydrocarbyl linker. For example, the clay or shale stabilizer can have the structure:

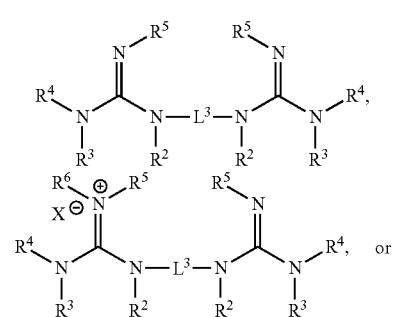

-continued

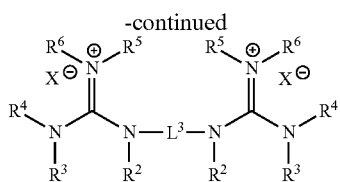

The variables $R^2$, $R^3$, $R^4$, $R^5$, and $R^6$ can be each independently selected from —H, halogen, an organic group, and substituted or unsubstituted $(C_1-C_{30})$hydrocarbyl interrupted by 0, 1, 2, or 3 of at least one of —O—, —S—, and substituted or unsubstituted —NH—, or at least one pair of $R^2$, $R^3$, $R^4$, $R^5$, and $R^6$ together can form a substituted or unsubstituted $(C_2-C_{20})$hydrocarbylene such that at least two of the nitrogen atoms in the clay or shale stabilizer are part of a heterocycle including the substituted or unsubstituted $(C_2-C_{20})$hydrocarbylene. Optionally, at least one of $R^2$, $R^3$, $R^4$, $R^5$, and $R^6$ can be bonded to at least one $R^2$, $R^3$, $R^4$, $R^5$, and $R^6$ on a different guanidine or guanidinium group in the same clay or shale stabilizer. The variable $X^-$ is a counterion. The variable $L^3$ is a substituted or unsubstituted $(C_1-C_{30})$hydrocarbyl interrupted by 0, 1, 2, or 3 of at least one of —O—, —S—, and substituted or unsubstituted —NH—. The variable $L^3$ can be $(C_2-C_{20})$alkyl. The clay or shale stabilizer can be 1,6-hexamethylene-bis-guanidine or 1,6-hexamethylene-bis-cyanoguanidine.

In some embodiments, $R^1$ can be -$L^1$-C(O)$R^7$. In some embodiments, the clay or shale stabilizer has the structure:

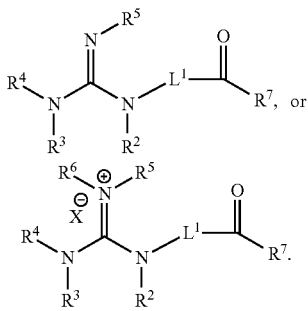

The variable $L^1$ can be selected from the group consisting of a bond, a substituted or unsubstituted $(C_1-C_{30})$hydrocarbylene interrupted by 0, 1, 2, or 3 of at least one of —O—, —S—, and substituted or unsubstituted —NH—. Optionally, $L^1$ can include a bond to at least one $R^1$, $R^2$, $R^3$, $R^4$, $R^5$, and $R^6$ on a different guanidine or guanidinium group in the same clay or shale stabilizer. The variable $L^1$ can be a $(C_1-C_{30})$hydrocarbylene interrupted by 0, 1, 2, or 3 of at least one of —O—, —S—, and substituted or unsubstituted —NH— and including at least one —NH$_2$ substituent. The variable $L^1$ can be a $(C_1-C_{15})$alkylene including at least one —NH$_2$ substituent. The variable $L^1$ can be a butylene including at least one —NH$_2$ substituent. The variable $L^1$ can be —(CH$_2$)$_3$—CH(NH$_2$)—. The variable $R^7$ can be selected from the group consisting of —OH, —OR$^8$, —O$^-$Y$^+$, —O$^-$, and a bond to at least one $R^1$, $R^2$, $R^3$, $R^4$, $R^5$, and $R^6$ on a different guanidine or guanidinium group in the same clay or shale stabilizer. The variable $R^8$ can be a substituted or unsubstituted $(C_1-C_{50})$hydrocarbyl interrupted by 0, 1, 2, or 3 of at least one of —O—, —S—, and substituted or unsubstituted —NH—. The variable $R^8$ can be a $(C_1-C_{50})$ alkyl. The variable $R^8$ can be a $(C_1-C_{15})$alkyl. The variable $R^8$ can be a $(C_1-C_5)$alkyl. The variable $R^8$ can be ethyl. The variable $Y^+$ is a counterion, such as any suitable cationic counterion, such as selected from the group consisting of Na$^+$, K$^+$, Li$^+$, H$^+$, NH$_4^+$, Ca$^{2+}$, Mg$^{2+}$, Zn$^{2+}$, and Al$^{3+}$.

In some embodiments, the clay or shale stabilizer can be a polymer including repeating units having the structure:

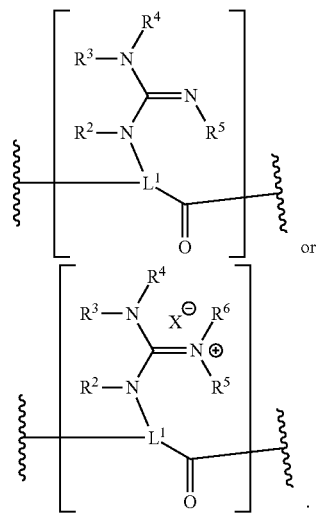

In some embodiments, the clay or shale stabilizer has the structure:

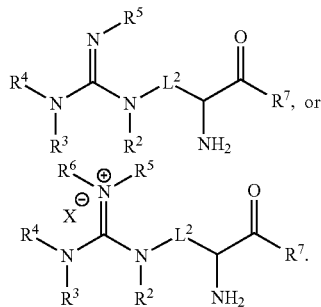

The variable $L^2$ can be selected from the group consisting of a bond and a substituted or unsubstituted $(C_1-C_{28})$hydrocarbylene interrupted by 0, 1, 2, or 3 of at least one of —O—, —S—, and substituted or unsubstituted —NH—. The variable $L^2$ can be a $(C_1-C_{15})$alkylene. The variable $L^2$ can be a propylene. The variable $L^2$ can be —(CH$_2$)$_3$—.

The clay or shale stabilizer can be a polymer including repeating units having the structure:

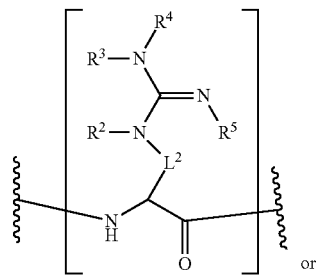

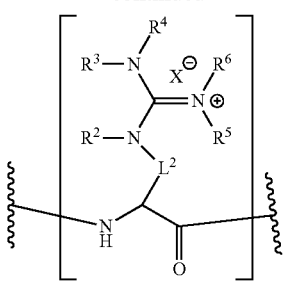

In some embodiments, the clay or shale stabilizer has the structure:

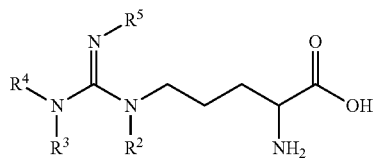

or a salt thereof,

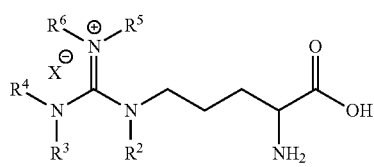

or a salt thereof, or

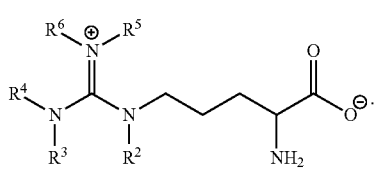

The clay or shale stabilizer can be a polymer including repeating units having the structure:

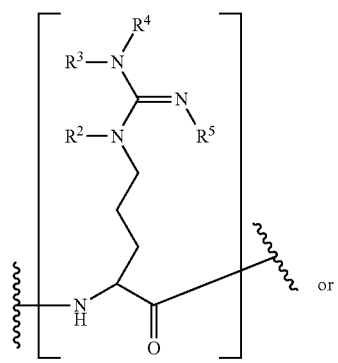

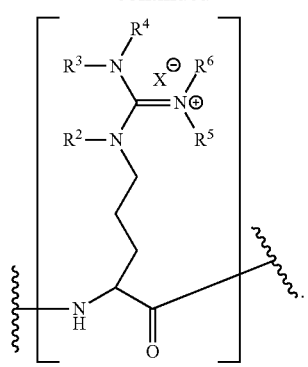

In some embodiments, the clay or shale stabilizer is L or D (or any suitable mixture of L and D) arginine or a salt thereof, a guanidinium form of the arginine or a salt thereof, or is a zwitterionic form of the arginine with a guanidinium and a carboxylate ion. In some embodiments, the clay or shale stabilizer is a polyarginine, or polymer including arginine repeating units (e.g., any suitable protein including an arginine unit). The clay or shale stabilizer can have the structure:

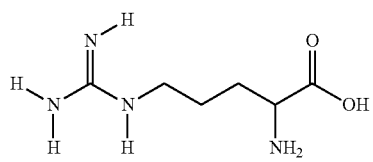

or a salt thereof,

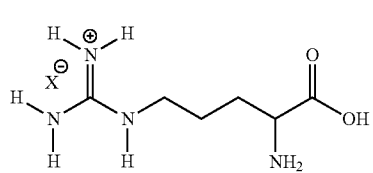

or a salt thereof, or

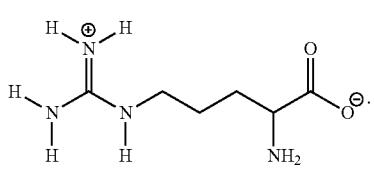 [SMILES: NC(=[NH2+])NCCCC(N)C(=O)[O-]]

The clay or shale stabilizer can be a polymer including repeating units having the structure:

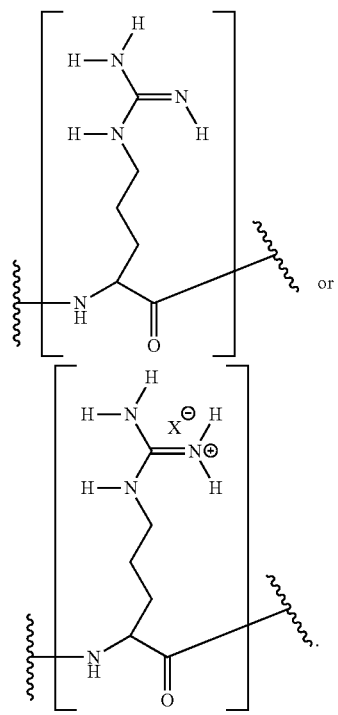

In some embodiments, the clay or shale stabilizer is L-arginine or a salt thereof, a guanidinium form of L-arginine or a salt thereof, or is a zwitterionic form of L-arginine with a guanidinium and a carboxylate ion. The clay or shale stabilizer can have the structure:

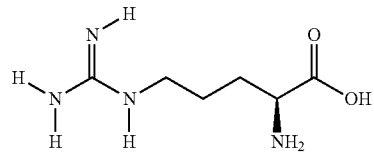 [SMILES: [H]/N=C(/N)NCCC[C@H](N)C(=O)O]

or a salt thereof,

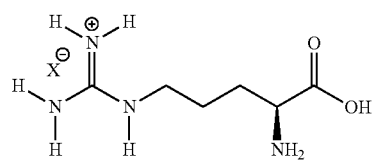

or a salt thereof, or

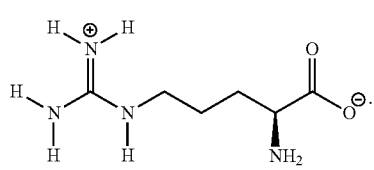

The clay or shale stabilizer can be a polymer including repeating units having the structure:

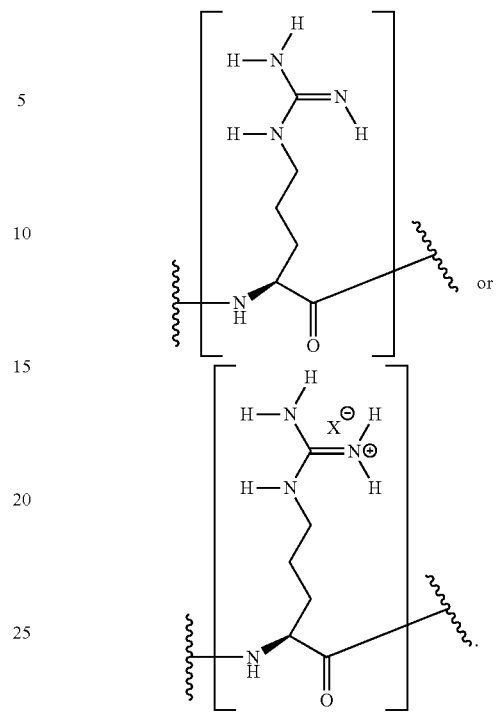

In some embodiments, the clay or shale stabilizer is an ester of L or D (or any suitable mixture of L and D) arginine, or an ester of a guanidinium form of the arginine. The clay or shale stabilizer can have the structure:

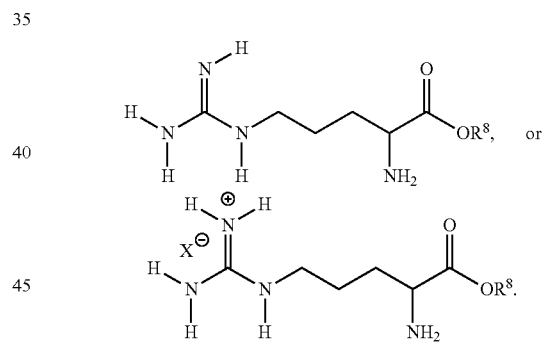

The variable $R^8$ can be a substituted or unsubstituted $(C_1\text{-}C_{50})$hydrocarbyl interrupted by 0, 1, 2, or 3 of at least one of —O—, —S—, and substituted or unsubstituted —NH—. The variable $R^8$ can be a $(C_1\text{-}C_{50})$alkyl. The variable $R^8$ can be a $(C_1\text{-}C_{15})$alkyl. The variable $R^8$ can be a $(C_1\text{-}C_5)$alkyl. The variable $R^8$ can be ethyl.

In some embodiments, the clay or shale stabilizer is an ester of L-arginine, or an ester of a guanidinium form of L-arginine. The clay or shale stabilizer can have the structure:

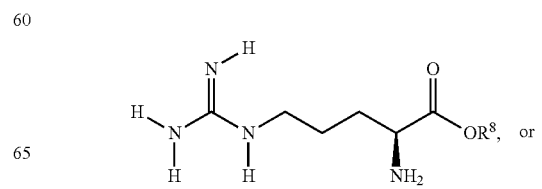

-continued

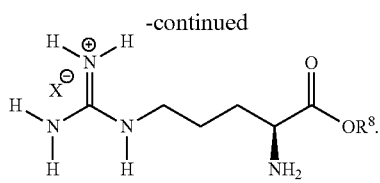

The variable $R^8$ can be a substituted or unsubstituted ($C_1$-$C_{50}$)hydrocarbyl interrupted by 0, 1, 2, or 3 of at least one of —O—, —S—, and substituted or unsubstituted —NH—. The variable $R^8$ can be a ($C_1$-$C_{50}$)alkyl. The variable $R^8$ can be a ($C_1$-$C_{15}$)alkyl. The variable $R^8$ can be a ($C_1$-$C_5$)alkyl. The variable $R^8$ can be ethyl.

Other Components.

The composition including the clay or shale stabilizer, or a mixture including the composition, can include any suitable additional component in any suitable proportion, such that the composition, or mixture including the same, can be used as described herein.

In some embodiments, the composition includes one or more second clay or shale stabilizers. The second clay or shale stabilizer can be any suitable clay or shale stabilizer. In various embodiments, the second clay or shale stabilizer can be a substituted or unsubstituted amine (e.g., triethylamine), potassium chloride, a crosslinked polyvinylpyrrolidone, an inorganic phosphate (e.g., as described in U.S. Pat. No. 4,605,068), a polyalkoxy diamine or a salt thereof (e.g., as described in U.S. Pat. Nos. 6,484,821; 6,609,578; 6,247,543; and U.S. Patent Publication No. 20030106718), choline or a choline derivative (e.g., as described in U.S. Pat. No. 5,908,814), an oligomethylene diamine or a salt thereof (e.g., as described in U.S. Pat. No. 5,771,971 and U.S. Patent Publication No. 20020155956), an addition product of carboxymethyl cellulose and an organic amine (e.g., as described in WO 2006/013595), 1,2-cyclohexanediamine or a salt thereof (e.g., as described in WO 2006/013597), a salt of a phosphoric acid ester of an oxyalkylated polyol (e.g., as described in WO 2006/013597), a combination of a partially hydrolyzed acrylic copolymer potassium chloride and polyanionic cellulose (e.g., as described in U.S. Pat. No. 4,664,818), a quaternary ammonium compound (e.g., as described in U.S. Pat. Nos. 5,197,544 and 5,380,706), a polymer based on dialkyl aminoalkyl methacrylate (e.g., as described in U.S. Pat. No. 7,091,159), an aqueous solution containing a polymer with hydrophilic and hydrophobic groups (e.g., as described in U.S. Pat. No. 5,728,653), and a reaction product of a polyhydroxyalkane and an alkylene oxide (e.g., as described in U.S. Pat. No. 6,544,933), and PERFORMATROL® shale stabilizer. In some embodiments, the second clay or shale stabilizer can be about 0.000.1 wt % to about 50 wt % of the composition, about 0.000.1 wt % to about 10 wt %, about 0.004 wt % to about 0.01 wt % of the composition, or about 0.000.1 wt % or less, 0.000.5 wt %, 0.001, 0.005, 0.01, 0.05, 0.1, 0.5, 1, 2, 3, 4, 5, 6, 7, 8, 9, or about 10 wt % or more of the composition.

In some embodiments, the composition includes one or more viscosifiers. The viscosifier can be any suitable viscosifier. The viscosifier can affect the viscosity of the composition or a solvent that contacts the composition at any suitable time and location. In some embodiments, the viscosifier provides an increased viscosity at least one of before injection into the subterranean formation, at the time of injection into the subterranean formation, during travel through a tubular disposed in a borehole, once the composition reaches a particular subterranean location, or some period of time after the composition reaches a particular subterranean location. In some embodiments, the viscosifier can be about 0.000.1 wt % to about 10 wt % of the composition, about 0.004 wt % to about 0.01 wt % of the composition, or about 0.000.1 wt % or less, 0.000.5 wt %, 0.001, 0.005, 0.01, 0.05, 0.1, 0.5, 1, 2, 3, 4, 5, 6, 7, 8, 9, or about 10 wt % or more of the composition.

The viscosifier can include at least one of a substituted or unsubstituted polysaccharide, and a substituted or unsubstituted polyalkene (e.g., a polyethylene, wherein the ethylene unit is substituted or unsubstituted, derived from the corresponding substituted or unsubstituted ethene), wherein the polysaccharide or polyalkene is crosslinked or uncrosslinked. The viscosifier can include a polymer including at least one repeating unit derived from a monomer selected from the group consisting of ethylene glycol, acrylamide, vinyl acetate, 2-acrylamidomethylpropane sulfonic acid or its salts, trimethylammoniumethyl acrylate halide, and trimethylammoniumethyl methacrylate halide. The viscosifier can include a crosslinked gel or a crosslinkable gel. The viscosifier can include at least one of a linear polysaccharide and a poly(($C_2$-$C_{10}$)alkene), wherein the ($C_2$-$C_{10}$)alkene is substituted or unsubstituted. The viscosifier can include at least one of poly(acrylic acid) or ($C_1$-$C_5$)alkyl esters thereof, poly(methacrylic acid) or ($C_1$-$C_5$)alkyl esters thereof, poly (vinyl acetate), poly(vinyl alcohol), poly(ethylene glycol), poly(vinyl pyrrolidone), polyacrylamide, poly (hydroxyethyl methacrylate), alginate, chitosan, curdlan, dextran, emulsan, a galactoglucopolysaccharide, gellan, glucuronan, N-acetyl-glucosamine, N-acetyl-heparosan, hyaluronic acid, kefiran, lentinan, levan, mauran, pullulan, scleroglucan, schizophyllan, stewartan, succinoglycan, xanthan, diutan, welan, derivatized starch, tamarind, tragacanth, guar gum, derivatized guar (e.g., hydroxypropyl guar, carboxy methyl guar, or carboxymethyl hydroxypropyl guar), gum ghatti, gum arabic, locust bean gum, and derivatized cellulose (e.g., carboxymethyl cellulose, hydroxyethyl cellulose, carboxymethyl hydroxyethyl cellulose, hydroxypropyl cellulose, or methyl hydroxy ethyl cellulose).

In some embodiments, the viscosifier can include at least one of a poly(vinyl alcohol) homopolymer, poly(vinyl alcohol) copolymer, a crosslinked poly(vinyl alcohol) homopolymer, and a crosslinked poly(vinyl alcohol) copolymer. The viscosifier can include a poly(vinyl alcohol) copolymer or a crosslinked poly(vinyl alcohol) copolymer including at least one of a graft, linear, branched, block, and random copolymer of vinyl alcohol and at least one of a substituted or unsubstituted ($C_2$-$C_{50}$)hydrocarbyl having at least one aliphatic unsaturated C≡C bond therein, and a substituted or unsubstituted ($C_2$-$C_{50}$)alkene. The viscosifier can include a poly(vinyl alcohol) copolymer or a crosslinked poly(vinyl alcohol) copolymer including at least one of a graft, linear, branched, block, and random copolymer of vinyl alcohol and at least one of vinyl phosphonic acid, vinylidene diphosphonic acid, substituted or unsubstituted 2-acrylamido-2-methylpropanesulfonic acid, a substituted or unsubstituted ($C_1$-$C_{20}$)alkenoic acid, propenoic acid, butenoic acid, pentenoic acid, hexenoic acid, octenoic acid, nonenoic acid, decenoic acid, acrylic acid, methacrylic acid, hydroxypropyl acrylic acid, acrylamide, fumaric acid, methacrylic acid, hydroxypropyl acrylic acid, vinyl phosphonic acid, vinylidene diphosphonic acid, itaconic acid, crotonic acid, mesoconic acid, citraconic acid, styrene sulfonic acid, allyl sulfonic acid, methallyl sulfonic acid, vinyl sulfonic acid, and a substituted or unsubstituted ($C_1$-$C_{20}$)alkyl ester thereof. The viscosifier can include a poly(vinyl alcohol) copolymer or a crosslinked poly(vinyl alcohol) copolymer including at least one of a graft, linear, branched, block, and random copolymer of vinyl alcohol and at least one of vinyl acetate, vinyl propanoate, vinyl butanoate, vinyl pentanoate, vinyl hexanoate, vinyl 2-methyl butanoate, vinyl 3-ethylpentanoate, and vinyl 3-ethylhexanoate, maleic anhydride, a substituted or unsubstituted $(C_1-C_{20})$alkenoic substituted or unsubstituted $(C_1-C_{20})$alkanoic anhydride, a substituted or unsubstituted $(C_1-C_{20})$alkenoic substituted or unsubstituted $(C_1-C_{20})$alkenoic anhydride, propenoic acid anhydride, butenoic acid anhydride, pentenoic acid anhydride, hexenoic acid anhydride, octenoic acid anhydride, nonenoic acid anhydride, decenoic acid anhydride, acrylic acid anhydride, fumaric acid anhydride, methacrylic acid anhydride, hydroxypropyl acrylic acid anhydride, vinyl phosphonic acid anhydride, vinylidene diphosphonic acid anhydride, itaconic acid anhydride, crotonic acid anhydride, mesoconic acid anhydride, citraconic acid anhydride, styrene sulfonic acid anhydride, allyl sulfonic acid anhydride, methallyl sulfonic acid anhydride, vinyl sulfonic acid anhydride, and an N—$(C_1-C_{10})$alkenyl nitrogen containing substituted or unsubstituted $(C_1-C_{10})$heterocycle. The viscosifier can include a poly(vinyl alcohol) copolymer or a crosslinked poly(vinyl alcohol) copolymer including at least one of a graft, linear, branched, block, and random copolymer that includes a poly(vinylalcohol/acrylamide) copolymer, a poly (vinylalcohol/2-acrylamido-2-methylpropanesulfonic acid) copolymer, a poly (acrylamide/2-acrylamido-2-methylpropanesulfonic acid) copolymer, or a poly(vinylalcohol/N-vinylpyrrolidone) copolymer. The viscosifier can include a crosslinked poly(vinyl alcohol) homopolymer or copolymer including a crosslinker including at least one of chromium, aluminum, antimony, zirconium, titanium, calcium, boron, iron, silicon, copper, zinc, magnesium, and an ion thereof. The viscosifier can include a crosslinked poly(vinyl alcohol) homopolymer or copolymer including a crosslinker including at least one of an aldehyde, an aldehyde-forming compound, a carboxylic acid or an ester thereof, a sulfonic acid or an ester thereof, a phosphonic acid or an ester thereof, an acid anhydride, and an epihalohydrin.

In various embodiments, the composition can include one or more crosslinkers. The crosslinker can be any suitable crosslinker. In some examples, the crosslinker can be incorporated in a crosslinked viscosifier, and in other examples, the crosslinker can crosslink a crosslinkable material (e.g., downhole). The crosslinker can include at least one of chromium, aluminum, antimony, zirconium, titanium, calcium, boron, iron, silicon, copper, zinc, magnesium, and an ion thereof. The crosslinker can include at least one of boric acid, borax, a borate, a $(C_1-C_{30})$hydrocarbylboronic acid, a $(C_1-C_{30})$hydrocarbyl ester of a $(C_1-C_{30})$hydrocarbylboronic acid, a $(C_1-C_{30})$hydrocarbylboronic acid-modified polyacrylamide, ferric chloride, disodium octaborate tetrahydrate, sodium metaborate, sodium diborate, sodium tetraborate, disodium tetraborate, a pentaborate, ulexite, colemanite, magnesium oxide, zirconium lactate, zirconium triethanol amine, zirconium lactate triethanolamine, zirconium carbonate, zirconium acetylacetonate, zirconium malate, zirconium citrate, zirconium diisopropylamine lactate, zirconium glycolate, zirconium triethanol amine glycolate, zirconium lactate glycolate, titanium lactate, titanium malate, titanium citrate, titanium ammonium lactate, titanium triethanolamine, titanium acetylacetonate, aluminum lactate, and aluminum citrate. In some embodiments, the crosslinker can be a $(C_1-C_{20})$alkylenebiacrylamide (e.g., methylenebisacrylamide), a poly$((C_1-C_{20})$alkenyl)-substituted mono- or poly-$(C_1-C_{20})$alkyl ether (e.g., pentaerythritol allyl ether), and a poly$(C_2-C_{20})$alkenylbenzene (e.g., divinylbenzene). In some embodiments, the crosslinker can be at least one of alkyl diacrylate, ethylene glycol diacrylate, ethylene glycol dimethacrylate, polyethylene glycol diacrylate, polyethylene glycol dimethacrylate, ethoxylated bisphenol A diacrylate, ethoxylated bisphenol A dimethacrylate, ethoxylated trimethylol propane triacrylate, ethoxylated trimethylol propane trimethacrylate, ethoxylated glyceryl triacrylate, ethoxylated glyceryl trimethacrylate, ethoxylated pentaerythritol tetraacrylate, ethoxylated pentaerythritol tetramethacrylate, ethoxylated dipentaerythritol hexaacrylate, polyglyceryl monoethylene oxide polyacrylate, polyglyceryl polyethylene glycol polyacrylate, dipentaerythritol hexaacrylate, dipentaerythritol hexamethacrylate, neopentyl glycol diacrylate, neopentyl glycol dimethacrylate, pentaerythritol triacrylate, pentaerythritol trimethacrylate, trimethylol propane triacrylate, trimethylol propane trimethacrylate, tricyclodecane dimethanol diacrylate, tricyclodecane dimethanol dimethacrylate, 1,6-hexanediol diacrylate, and 1,6-hexanediol dimethacrylate. The crosslinker can be about 0.000.01 wt % to about 5 wt % of the composition, about 0.001 wt % to about 0.01 wt %, or about 0.000.01 wt % or less, or about 0.000.05 wt %, 0.000,1, 0.000,5, 0.001, 0.005, 0.01, 0.05, 0.1, 0.5, 1, 2, 3, 4, or about 5 wt % or more.

In some embodiments, the composition can include one or more breakers. The breaker can be any suitable breaker, such that the surrounding fluid (e.g., a fracturing fluid) can be at least partially broken for more complete and more efficient recovery thereof, such as at the conclusion of the hydraulic fracturing treatment. In some embodiments, the breaker can be encapsulated or otherwise formulated to give a delayed-release or a time-release of the breaker, such that the surrounding liquid can remain viscous for a suitable amount of time prior to breaking. The breaker can be any suitable breaker; for example, the breaker can be a compound that includes a $Na^+$, $K^+$, $Li^+$, $NH_4^+$, $Fe^{2+}$, $Fe^{3+}$, $Cu^{1+}$, $Cu^{2+}$, $Ca^{2+}$, $Mg^{2+}$, $Zn^{2+}$, and an $Al^{3+}$ salt of a chloride, fluoride, bromide, phosphate, or sulfate ion. In some examples, the breaker can be an oxidative breaker or an enzymatic breaker. An oxidative breaker can be at least one of a $Na^+$, $K^+$, $Li^+$, $NH_{4+}$, $Fe^{2+}$, $Fe^{3+}$, $Cu^{1+}$, $Cu^{2+}$, $Ca^{2+}$, $Mg^{2+}$, $Zn^{2+}$, and an $Al^{3+}$ salt of a persulfate, percarbonate, perborate, peroxide, perphosphate, permanganate, chlorite, or hyporchlorite ion. An enzymatic breaker can be at least one of an alpha or beta amylase, amyloglucosidase, oligoglucosidase, invertase, maltase, cellulase, hemi-cellulase, and mannanohydrolase. The breaker can be about 0.001 wt % to about 30 wt % of the composition, or about 0.01 wt % to about 5 wt %, or about 0.001 wt % or less, or about 0.005 wt %, 0.01, 0.05, 0.1, 0.5, 1, 2, 3, 4, 5, 6, 8, 10, 12, 14, 16, 18, 20, 22, 24, 26, 28, or about 30 wt % or more.

The composition, or a mixture including the composition, can include any suitable fluid. For example, the fluid can be at least one of crude oil, dipropylene glycol methyl ether, dipropylene glycol dimethyl ether, dipropylene glycol methyl ether, dipropylene glycol dimethyl ether, dimethyl formamide, diethylene glycol methyl ether, ethylene glycol butyl ether, diethylene glycol butyl ether, butylglycidyl ether, propylene carbonate, D-limonene, a $C_2-C_{40}$ fatty acid $C_1-C_{10}$ alkyl ester (e.g., a fatty acid methyl ester), tetrahydrofurfuryl methacrylate, tetrahydrofurfuryl acrylate, 2-butoxy ethanol, butyl acetate, butyl lactate, furfuryl acetate, dimethyl sulfoxide, dimethyl formamide, a petroleum distillation product of fraction (e.g., diesel, kerosene, napthas, and the like) mineral oil, a hydrocarbon oil, a hydrocarbon including an aromatic carbon-carbon bond (e.g., benzene, toluene), a hydrocarbon including an alpha olefin, xylenes, an ionic liquid, methyl ethyl ketone, an ester of oxalic, maleic or succinic acid, methanol, ethanol, propanol (iso- or normal-), butyl alcohol (iso-, tert-, or normal-), an aliphatic hydrocarbon (e.g., cyclohexanone, hexane), water, brine, produced water, flowback water, brackish water, and sea water. The fluid can form about 0.001 wt % to about 99.999 wt % of the composition, or a mixture including the same, or about 0.001 wt % or less, 0.01 wt %, 0.1, 1, 2, 3, 4, 5, 6, 8, 10, 15, 20, 25, 30, 35, 40, 45, 50, 55, 60, 65, 70, 75, 80, 85, 90, 95, 96, 97, 98, 99, 99.9, 99.99, or about 99.999 wt % or more.

The composition including the clay or shale stabilizer can include any suitable downhole fluid. The composition including the clay or shale stabilizer can be combined with any suitable downhole fluid before, during, or after the placement of the composition in the subterranean formation or the contacting of the composition and the subterranean material. In some examples, the composition including the clay or shale stabilizer is combined with a downhole fluid above the surface, and then the combined composition is placed in a subterranean formation or contacted with a subterranean material. In another example, the composition including the clay or shale stabilizer is injected into a subterranean formation to combine with a downhole fluid, and the combined composition is contacted with a subterranean material or is considered to be placed in the subterranean formation. In various examples, at least one of prior to, during, and after the placement of the composition in the subterranean formation or contacting of the subterranean material and the composition, the composition is used in the subterranean formation (e.g., downhole), at least one of alone and in combination with other materials, as a drilling fluid, stimulation fluid, fracturing fluid, spotting fluid, clean-up fluid, completion fluid, remedial treatment fluid, abandonment fluid, pill, acidizing fluid, cementing fluid, packer fluid, or a combination thereof.

In various embodiments, the composition including the clay or shale stabilizer, or a mixture including the same, can include any suitable downhole fluid, such as an aqueous or oil-based fluid including a drilling fluid, stimulation fluid, fracturing fluid, spotting fluid, clean-up fluid, completion fluid, remedial treatment fluid, abandonment fluid, pill, acidizing fluid, cementing fluid, packer fluid, or a combination thereof. The placement of the composition in the subterranean formation can include contacting the subterranean material and the mixture. Any suitable weight percent of the composition or of a mixture including the same that is placed in the subterranean formation or contacted with the subterranean material can be the downhole fluid, such as about 0.001 wt % to about 99.999 wt %, about 0.01 wt % to about 99.99 wt %, about 0.1 wt % to about 99.9 wt %, about 20 wt % to about 90 wt %, or about 0.001 wt % or less, or about 0.01 wt %, 0.1, 1, 2, 3, 4, 5, 10, 15, 20, 30, 40, 50, 60, 70, 80, 85, 90, 91, 92, 93, 94, 95, 96, 97, 98, 99, 99.9, 99.99 wt %, or about 99.999 wt % or more of the composition or mixture including the same.

In some embodiments, the composition, or a mixture including the same, can include any suitable amount of any suitable material used in a downhole fluid. For example, the composition or a mixture including the same can include water, saline, aqueous base, acid, oil, organic solvent, synthetic fluid oil phase, aqueous solution, alcohol or polyol, cellulose, starch, alkalinity control agents, acidity control agents, density control agents, density modifiers, emulsifiers, dispersants, polymeric stabilizers, crosslinking agents, polyacrylamide, a polymer or combination of polymers, antioxidants, heat stabilizers, foam control agents, solvents, diluents, plasticizer, filler or inorganic particle, pigment, dye, precipitating agent, rheology modifier, oil-wetting agents, set retarding additives, surfactants, gases, weight reducing additives, heavy-weight additives, lost circulation materials, filtration control additives, salts (e.g., any suitable salt, such as potassium salts such as potassium chloride, potassium bromide, potassium formate; calcium salts such as calcium chloride, calcium bromide, calcium formate; cesium salts such as cesium chloride, cesium bromide, cesium formate, or a combination thereof), fibers, thixotropic additives, breakers, crosslinkers, rheology modifiers, curing accelerators, curing retarders, pH modifiers, chelating agents, scale inhibitors, enzymes, resins, water control materials, oxidizers, markers, Portland cement, pozzolana cement, gypsum cement, high alumina content cement, slag cement, silica cement, fly ash, metakaolin, shale, zeolite, a crystalline silica compound, amorphous silica, hydratable clays, microspheres, lime, or a combination thereof. In various embodiments, the composition or a mixture including the same can include one or more additive components such as: COLDTROL®, ATC®, OMC 2™, and OMC 42™ thinner additives; RHEMOD™ viscosifier and suspension agent; TEMPERUS™ and VIS-PLUS® additives for providing temporary increased viscosity; TAU-MOD™ viscosifying/suspension agent; ADAPTA®, DURATONE® HT, THERMO TONE™, BDF™-366, and BDF™-454 filtration control agents; LIQUITONE™ polymeric filtration agent and viscosifier; FACTANT™ emulsion stabilizer; LE SUPERMUL™, EZ MUL® NT, and FORTI-MUL® emulsifiers; DRIL TREAT® oil wetting agent for heavy fluids; BARACARB® bridging agent; BAROID® weighting agent; BAROLIFT® hole sweeping agent; SWEEP-WATE® sweep weighting agent; BDF-508 rheology modifier; and GELTONE® II organophilic clay. In various embodiments, the composition or a mixture including the same can include one or more additive components such as: X-TEND® II, PAC™-R, PAC™-L, LIQUI-VIS® EP, BRINEDRIL-VIS™, BARAZAN®, N-VIS®, and AQUA-GEL® viscosifiers; THERMA-CHEK®, N-DRIL™, N-DRIL™ HT PLUS, IMPERMEX®, FILTERCHEK™, DEXTRID®, CARBONOX®, and BARANEX® filtration control agents; PERFORMATROL®, GEM™, EZ-MUD®, CLAY GRABBER®, CLAYSEAL®, CRYSTAL-DRIL®, and CLAY SYNC™ II shale stabilizers; NXS-LUBE™, EP MUDLUBE®, and DRIL-N-SLIDE™ lubricants; QUIK-THIN®, IRON-THIN™, and ENVIRO-THIN™ thinners; SOURSCAV™ scavenger; BARACOR® corrosion inhibitor; and WALL-NUT®, SWEEP-WATE®, STOPPIT™, PLUG-GIT®, BARACARB®, DUO-SQUEEZE®, BARO-FIBRE™, STEELSEAL®, and HYDRO-PLUG® lost circulation management materials. Any suitable proportion of the composition or mixture including the composition can include any optional component listed in this paragraph, such as about 0.001 wt % to about 99.999 wt %, about 0.01 wt % to about 99.99 wt %, about 0.1 wt % to about 99.9 wt %, about 20 to about 90 wt %, or about 0.001 wt % or less, or about 0.01 wt %, 0.1, 1, 2, 3, 4, 5, 10, 15, 20, 30, 40, 50, 60, 70, 80, 85, 90, 91, 92, 93, 94, 95, 96, 97, 98, 99, 99.9, 99.99 wt %, or about 99.999 wt % or more of the composition or mixture.

A drilling fluid, also known as a drilling mud or simply "mud," is a specially designed fluid that is circulated through a wellbore as the wellbore is being drilled to facilitate the drilling operation. The drilling fluid can be water-based or oil-based. The drilling fluid can carry cuttings up from beneath and around the bit, transport them up the annulus, and allow their separation. Also, a drilling fluid can cool and lubricate the drill bit as well as reduce friction between the drill string and the sides of the hole. The drilling fluid aids in support of the drill pipe and drill bit, and provides a hydrostatic head to maintain the integrity of the wellbore walls and prevent well blowouts. Specific drilling fluid systems can be selected to optimize a drilling operation in accordance with the characteristics of a particular geological formation. The drilling fluid can be formulated to prevent unwanted influxes of formation fluids from permeable rocks and also to form a thin, low permeability filter cake that temporarily seals pores, other openings, and formations penetrated by the bit. In water-based drilling fluids, solid particles are suspended in a water or brine solution containing other components. Oils or other non-aqueous liquids can be emulsified in the water or brine or at least partially solubilized (for less hydrophobic non-aqueous liquids), but water is the continuous phase. A drilling fluid can be present in the mixture with the composition including the clay or shale stabilizer in any suitable amount, such as about 1 wt % or less, about 2 wt %, 3, 4, 5, 10, 15, 20, 30, 40, 50, 60, 70, 80, 85, 90, 95, 96, 97, 98, 99, 99.9, 99.99, or about 99.999 wt % or more of the mixture.

A water-based drilling fluid in embodiments of the present invention can be any suitable water-based drilling fluid. In various embodiments, the drilling fluid can include at least one of water (fresh or brine), a salt (e.g., calcium chloride, sodium chloride, potassium chloride, magnesium chloride, calcium bromide, sodium bromide, potassium bromide, calcium nitrate, sodium formate, potassium formate, cesium formate), aqueous base (e.g., sodium hydroxide or potassium hydroxide), alcohol or polyol, cellulose, starches, alkalinity control agents, density control agents such as a density modifier (e.g., barium sulfate), surfactants (e.g., betaines, alkali metal alkylene acetates, sultaines, ether carboxylates), emulsifiers, dispersants, polymeric stabilizers, crosslinking agents, polyacrylamides, polymers or combinations of polymers, antioxidants, heat stabilizers, foam control agents, solvents, diluents, plasticizers, filler or inorganic particles (e.g., silica), pigments, dyes, precipitating agents (e.g., silicates or aluminum complexes), and rheology modifiers such as thickeners or viscosifiers (e.g., xanthan gum). Any ingredient listed in this paragraph can be either present or not present in the mixture.

An oil-based drilling fluid or mud in embodiments of the present invention can be any suitable oil-based drilling fluid. In various embodiments the drilling fluid can include at least one of an oil-based fluid (or synthetic fluid), saline, aqueous solution, emulsifiers, other agents or additives for suspension control, weight or density control, oil-wetting agents, fluid loss or filtration control agents, and rheology control agents. An oil-based or invert emulsion-based drilling fluid can include between about 10:90 to about 95:5, or about 50:50 to about 95:5, by volume of oil phase to water phase. A substantially all oil mud includes about 100% liquid phase oil by volume (e.g., substantially no internal aqueous phase).

A pill is a relatively small quantity (e.g., less than about 500 bbl, or less than about 200 bbl) of drilling fluid used to accomplish a specific task that the regular drilling fluid cannot perform. For example, a pill can be a high-viscosity pill to, for example, help lift cuttings out of a vertical wellbore. In another example, a pill can be a freshwater pill to, for example, dissolve a salt formation. Another example is a pipe-freeing pill to, for example, destroy filter cake and relieve differential sticking forces. In another example, a pill is a lost circulation material pill to, for example, plug a thief zone. A pill can include any component described herein as a component of a drilling fluid.

A cement fluid can include an aqueous mixture of at least one of cement and cement kiln dust. The composition including the clay or shale stabilizer can form a useful combination with cement or cement kiln dust. The cement kiln dust can be any suitable cement kiln dust. Cement kiln dust can be formed during the manufacture of cement and can be partially calcined kiln feed that is removed from the gas stream and collected in a dust collector during a manufacturing process. Cement kiln dust can be advantageously utilized in a cost-effective manner since kiln dust is often regarded as a low value waste product of the cement industry. Some embodiments of the cement fluid can include cement kiln dust but no cement, cement kiln dust and cement, or cement but no cement kiln dust. The cement can be any suitable cement. The cement can be a hydraulic cement. A variety of cements can be utilized in accordance with embodiments of the present invention; for example, those including calcium, aluminum, silicon, oxygen, iron, or sulfur, which can set and harden by reaction with water. Suitable cements can include Portland cements, pozzolana cements, gypsum cements, high alumina content cements, slag cements, silica cements, and combinations thereof. In some embodiments, the Portland cements that are suitable for use in embodiments of the present invention are classified as Classes A, C, H, and G cements according to the American Petroleum Institute, *API Specification for Materials and Testing for Well Cements*, API Specification 10, Fifth Ed., Jul. 1, 1990. A cement can be generally included in the cementing fluid in an amount sufficient to provide the desired compressive strength, density, or cost. In some embodiments, the hydraulic cement can be present in the cementing fluid in an amount in the range of from 0 wt % to about 100 wt %, about 0 wt % to about 95 wt %, about 20 wt % to about 95 wt %, or about 50 wt % to about 90 wt %. A cement kiln dust can be present in an amount of at least about 0.01 wt %, or about 5 wt % to about 80 wt %, or about 10 wt % to about 50 wt %.

Optionally, other additives can be added to a cement or kiln dust-containing composition of embodiments of the present invention as deemed appropriate by one skilled in the art, with the benefit of this disclosure. Any optional ingredient listed in this paragraph can be either present or not present in the composition. For example, the composition can include fly ash, metakaolin, shale, zeolite, set retarding additive, surfactant, a gas, accelerators, weight reducing additives, heavy-weight additives, lost circulation materials, filtration control additives, dispersants, and combinations thereof. In some examples, additives can include crystalline silica compounds, amorphous silica, salts, fibers, hydratable clays, microspheres, pozzolan lime, thixotropic additives, combinations thereof, and the like.

In various embodiments, the composition or mixture can include a proppant, a resin-coated proppant, an encapsulated resin, or a combination thereof. A proppant is a material that keeps an induced hydraulic fracture at least partially open during or after a fracturing treatment. Proppants can be transported into the subterranean formation (e.g., downhole) to the fracture using fluid, such as fracturing fluid or another fluid. A higher-viscosity fluid can more effectively transport proppants to a desired location in a fracture, especially larger proppants, by more effectively keeping proppants in a suspended state within the fluid. Examples of proppants can include sand, gravel, glass beads, polymer beads, ground products from shells and seeds such as walnut hulls, and manmade materials such as ceramic proppant, bauxite, tetrafluoroethylene materials (e.g., TEFLON™ polytetrafluoroethylene), fruit pit materials, processed wood, composite particulates prepared from a binder and fine grade particulates such as silica, alumina, fumed silica, carbon black, graphite, mica, titanium dioxide, meta-silicate, calcium silicate, kaolin, talc, zirconia, boron, fly ash, hollow glass microspheres, and solid glass, or mixtures thereof. In some embodiments, the proppant can have an average particle size, wherein particle size is the largest dimension of a particle, of about 0.001 mm to about 3 mm, about 0.15 mm to about 2.5 mm, about 0.25 mm to about 0.43 mm, about 0.43 mm to about 0.85 mm, about 0.85 mm to about 1.18 mm, about 1.18 mm to about 1.70 mm, or about 1.70 to about 2.36 mm. In some embodiments, the proppant can have a distribution of particle sizes clustering around multiple averages, such as one, two, three, or four different average particle sizes. The composition or mixture can include any suitable amount of proppant, such as about 0.01 wt % to about 99.99 wt %, about 0.1 wt % to about 80 wt %, about 10 wt % to about 60 wt %, or about 0.01 wt % or less, or about 0.1 wt %, 1, 2, 3, 4, 5, 10, 15, 20, 30, 40, 50, 60, 70, 80, 85, 90, 91, 92, 93, 94, 95, 96, 97, 98, 99, about 99.9 wt %, or about 99.99 wt % or more.

The composition can include a payload material. The payload can be deposited in any suitable subterranean location. The method can include using the composition to deposit a payload material into a subterranean fracture. The subterranean fracture can be any suitable subterranean fracture. In some embodiments, the method includes forming the subterranean fracture; in other embodiments, the subterranean fracture is already formed. The payload material can be a proppant, or any other suitable payload material, such as a resin-coated proppant, a curable material, an encapsulated resin, a resin, a Portland cement, a pozzolana cement, a gypsum cement, a high alumina content cement, a slag cement, a silica cement, a cementitous kiln dust, fly ash, metakaolin, shale, zeolite, a set retarding additive, a corrosion inhibitor, a surfactant, a gas, an accelerator, a weight reducing additive, a heavy-weight additive, a lost circulation material, a filtration control additive, a dispersant, a crystalline silica compound, an amorphous silica, a salt, a fiber, a hydratable clay, a microsphere, pozzolan lime, a thixotropic additive, water, an aqueous base, an aqueous acid, an alcohol or polyol, a cellulose, a starch, an alkalinity control agent, an acidity control agent, a density control agent, a density modifier, an emulsifier, a polymeric stabilizer, a crosslinking agent, a polyacrylamide, a polymer or combination of polymers, an antioxidant, a heat stabilizer, a foam control agent, a solvent, a diluent, a plasticizer, a filler or inorganic particle, a pigment, a dye, a precipitating agent, a rheology modifier, or a combination thereof.

Drilling Assembly.

In various embodiments, the composition including the clay or shale stabilizer disclosed herein can directly or indirectly affect one or more components or pieces of equipment associated with the preparation, delivery, recapture, recycling, reuse, and/or disposal of the disclosed composition including the clay or shale stabilizer. For example, and with reference to FIG. 1, the disclosed composition including the clay or shale stabilizer can directly or indirectly affect one or more components or pieces of equipment associated with an exemplary wellbore drilling assembly 100, according to one or more embodiments. It should be noted that while FIG. 1 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 100 can include a drilling platform 102 that supports a derrick 104 having a traveling block 106 for raising and lowering a drill string 108. The drill string 108 can include drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the bit 114 rotates, it creates a wellbore 116 that penetrates various subterranean formations 118.

A pump 120 (e.g., a mud pump) circulates drilling fluid 122 through a feed pipe 124 and to the kelly 110, which conveys the drilling fluid 122 downhole through the interior of the drill string 108 and through one or more orifices in the drill bit 114. The drilling fluid 122 is then circulated back to the surface via an annulus 126 defined between the drill string 108 and the walls of the wellbore 116. At the surface, the recirculated or spent drilling fluid 122 exits the annulus 126 and can be conveyed to one or more fluid processing unit(s) 128 via an interconnecting flow line 130. After passing through the fluid processing unit(s) 128, a "cleaned" drilling fluid 122 is deposited into a nearby retention pit 132 (e.g., a mud pit). While illustrated as being arranged at the outlet of the wellbore 116 via the annulus 126, those skilled in the art will readily appreciate that the fluid processing unit(s) 128 can be arranged at any other location in the drilling assembly 100 to facilitate its proper function, without departing from the scope of the disclosure.

The composition including the clay or shale stabilizer can be added to the drilling fluid 122 via a mixing hopper 134 communicably coupled to or otherwise in fluid communication with the retention pit 132. The mixing hopper 134 can include mixers and related mixing equipment known to those skilled in the art. In other embodiments, however, the composition including the clay or shale stabilizer can be added to the drilling fluid 122 at any other location in the drilling assembly 100. In at least one embodiment, for example, there could be more than one retention pit 132, such as multiple retention pits 132 in series. Moreover, the retention pit 132 can be representative of one or more fluid storage facilities and/or units where the composition including the clay or shale stabilizer can be stored, reconditioned, and/or regulated until added to the drilling fluid 122.

As mentioned above, the composition including the clay or shale stabilizer can directly or indirectly affect the components and equipment of the drilling assembly 100. For example, the composition including the clay or shale stabilizer can directly or indirectly affect the fluid processing unit(s) 128, which can include one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, or any fluid reclamation equipment. The fluid processing unit(s) 128 can further include one or more sensors, gauges, pumps, compressors, and the like used to store, monitor, regulate, and/or recondition the composition including the clay or shale stabilizer.

The composition including the clay or shale stabilizer can directly or indirectly affect the pump 120, which representatively includes any conduits, pipelines, trucks, tubulars, and/or pipes used to fluidically convey the composition including the clay or shale stabilizer to the subterranean formation, any pumps, compressors, or motors (e.g., topside or downhole) used to drive the composition into motion, any valves or related joints used to regulate the pressure or flow rate of the composition, and any sensors (e.g., pressure, temperature, flow rate, and the like), gauges, and/or combinations thereof, and the like. The composition including the clay or shale stabilizer can also directly or indirectly affect the mixing hopper 134 and the retention pit 132 and their assorted variations.

The composition including the clay or shale stabilizer can also directly or indirectly affect the various downhole or subterranean equipment and tools that can come into contact with the composition including the clay or shale stabilizer such as the drill string 108, any floats, drill collars, mud motors, downhole motors, and/or pumps associated with the drill string 108, and any measurement while drilling (MWD)/logging while drilling (LWD) tools and related telemetry equipment, sensors, or distributed sensors associated with the drill string 108. The composition including the clay or shale stabilizer can also directly or indirectly affect any downhole heat exchangers, valves and corresponding actuation devices, tool seals, packers and other wellbore isolation devices or components, and the like associated with the wellbore 116. The composition including the clay or shale stabilizer can also directly or indirectly affect the drill bit 114, which can include roller cone bits, polycrystalline diamond compact (PDC) bits, natural diamond bits, any hole openers, reamers, coring bits, and the like.

While not specifically illustrated herein, the composition including the clay or shale stabilizer can also directly or indirectly affect any transport or delivery equipment used to convey the composition including the clay or shale stabilizer to the drilling assembly 100 such as, for example, any transport vessels, conduits, pipelines, trucks, tubulars, and/or pipes used to fluidically move the composition including the clay or shale stabilizer from one location to another, any pumps, compressors, or motors used to drive the composition into motion, any valves or related joints used to regulate the pressure or flow rate of the composition, and any sensors (e.g., pressure and temperature), gauges, and/or combinations thereof, and the like.

System or Apparatus.

In various embodiments, the present invention provides a system. The system can be any suitable system that can use or that can be generated by use of an embodiment of the composition described herein in a subterranean formation, or that can perform or be generated by performance of a method for using the composition described herein. The system can include a composition including the clay or shale stabilizer. The system can also include a subterranean formation including the composition therein. In some embodiments, the composition in the system can also include a downhole fluid, or the system can include a mixture of the composition and downhole fluid. In some embodiments, the system can include a tubular, and a pump configured to pump the composition into the subterranean formation through the tubular.

Various embodiments provide systems and apparatus configured for delivering the composition described herein to a subterranean location and for using the composition therein, such as for a drilling operation, a fracturing operation (e.g., pre-pad, pad, slurry, or finishing stages), a cementing operation, a completion operation, a logging operation, a spotting operation, or a packer operation. In various embodiments, the system or apparatus can include a pump fluidly coupled to a tubular (e.g., any suitable type of oilfield pipe, such as pipeline, drill pipe, production tubing, and the like), with the tubular containing a composition including the clay or shale stabilizer described herein.

In some embodiments, the system can include a drillstring disposed in a wellbore, with the drillstring including a drill bit at a downhole end of the drillstring. The system can also include an annulus between the drillstring and the wellbore. The system can also include a pump configured to circulate the composition through the drill string, through the drill bit, and back above-surface through the annulus. In some embodiments, the system can include a fluid processing unit configured to process the composition exiting the annulus to generate a cleaned drilling fluid for recirculation through the wellbore.

In various embodiments, the present invention provides an apparatus. The apparatus can be any suitable apparatus that can use the composition including the clay or shale stabilizer described herein in a subterranean formation, or that can perform or be generated by performance of a method for using the composition including the clay or shale stabilizer described herein.

The pump can be a high pressure pump in some embodiments. As used herein, the term "high pressure pump" will refer to a pump that is capable of delivering a fluid to a subterranean formation (e.g., downhole) at a pressure of about 1000 psi or greater. A high pressure pump can be used when it is desired to introduce the composition to a subterranean formation at or above a fracture gradient of the subterranean formation, but it can also be used in cases where fracturing is not desired. In some embodiments, the high pressure pump can be capable of fluidly conveying particulate matter, such as proppant particulates, into the subterranean formation. Suitable high pressure pumps will be known to one having ordinary skill in the art and can include floating piston pumps and positive displacement pumps.

In other embodiments, the pump can be a low pressure pump. As used herein, the term "low pressure pump" will refer to a pump that operates at a pressure of about 1000 psi or less. In some embodiments, a low pressure pump can be fluidly coupled to a high pressure pump that is fluidly coupled to the tubular. That is, in such embodiments, the low pressure pump can be configured to convey the composition to the high pressure pump. In such embodiments, the low pressure pump can "step up" the pressure of the composition before it reaches the high pressure pump.

In some embodiments, the systems or apparatuses described herein can further include a mixing tank that is upstream of the pump and in which the composition is formulated. In various embodiments, the pump (e.g., a low pressure pump, a high pressure pump, or a combination thereof) can convey the composition from the mixing tank or other source of the composition to the tubular. In other embodiments, however, the composition can be formulated offsite and transported to a worksite, in which case the composition can be introduced to the tubular via the pump directly from its shipping container (e.g., a truck, a railcar, a barge, or the like) or from a transport pipeline. In either case, the composition can be drawn into the pump, elevated to an appropriate pressure, and then introduced into the tubular for delivery to the subterranean formation.

Figure 2:
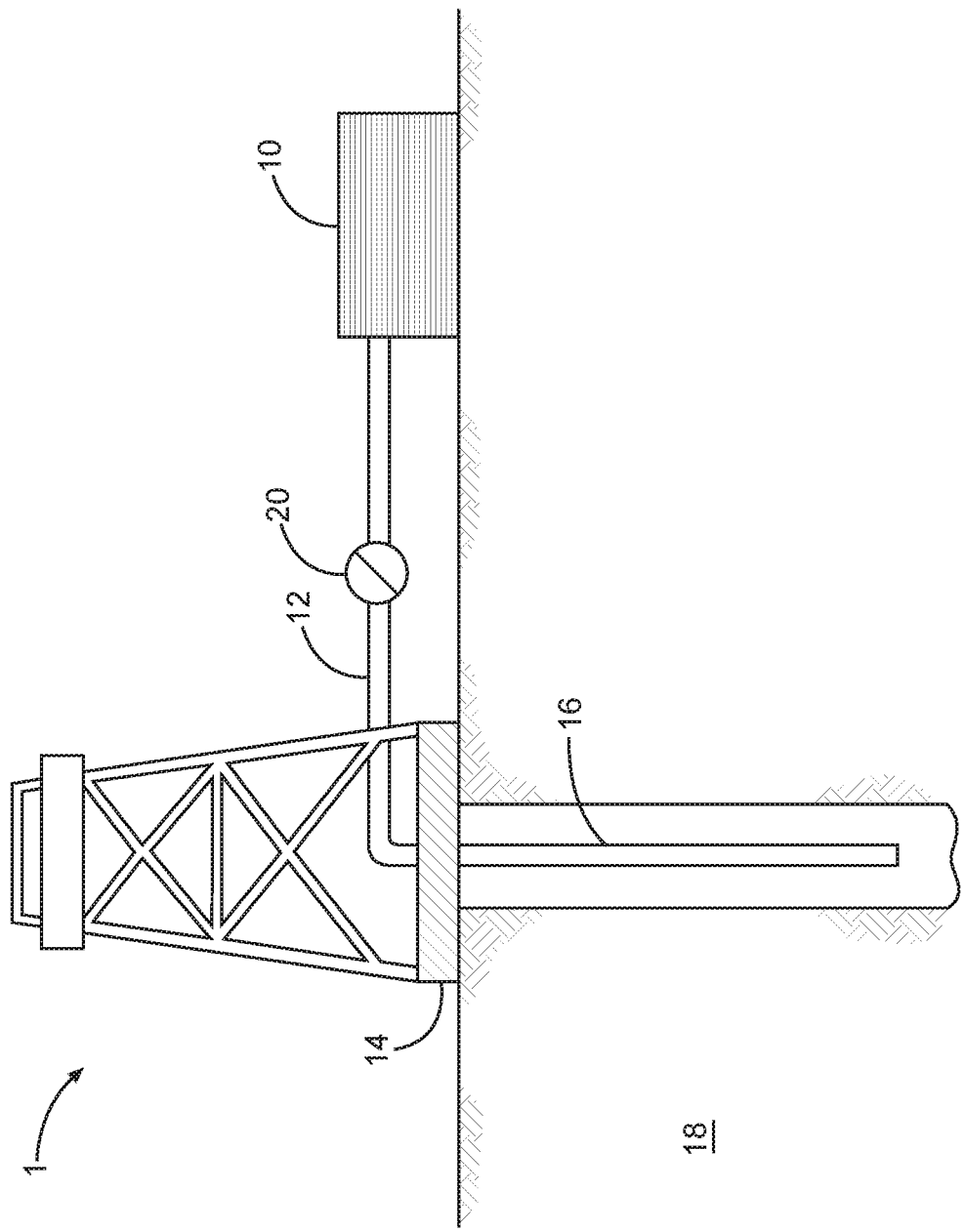
FIG. 2 illustrates a system or apparatus for delivering a composition to a subterranean formation, in accordance with various embodiments.

FIG. 2 shows an illustrative schematic of systems and apparatuses that can deliver embodiments of the compositions of the present invention to a subterranean location, according to one or more embodiments. It should be noted that while FIG. 2 generally depicts a land-based system or apparatus, it is to be recognized that like systems and apparatuses can be operated in subsea locations as well. Embodiments of the present invention can have a different scale than that depicted in FIG. 2. As depicted in FIG. 2, system or apparatus 1 can include mixing tank 10, in which an embodiment of the composition can be formulated. The composition can be conveyed via line 12 to wellhead 14, where the composition enters tubular 16, with tubular 16 extending from wellhead 14 into subterranean formation 18. Upon being ejected from tubular 16, the composition can subsequently penetrate into subterranean formation 18. Pump 20 can be configured to raise the pressure of the composition to a desired degree before its introduction into tubular 16. It is to be recognized that system or apparatus 1 is merely exemplary in nature and various additional components can be present that have not necessarily been depicted in FIG. 2 in the interest of clarity. In some examples, additional components that can be present include supply hoppers, valves, condensers, adapters, joints, gauges, sensors, compressors, pressure controllers, pressure sensors, flow rate controllers, flow rate sensors, temperature sensors, and the like.

Although not depicted in FIG. 2, at least part of the composition can, in some embodiments, flow back to wellhead 14 and exit subterranean formation 18. The composition that flows back can be substantially diminished in the concentration of the clay or shale stabilizer, or can have none of the clay or shale stabilizer therein. In some embodiments, the composition that has flowed back to wellhead 14 can subsequently be recovered, and in some examples reformulated, and recirculated to subterranean formation 18.

It is also to be recognized that the disclosed composition can also directly or indirectly affect the various downhole or subterranean equipment and tools that can come into contact with the composition during operation. Such equipment and tools can include wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, and the like), logging tools and related telemetry equipment, actuators (e.g., electromechanical devices, hydromechanical devices, and the like), sliding sleeves, production sleeves, plugs, screens, filters, flow control devices (e.g., inflow control devices, autonomous inflow control devices, outflow control devices, and the like), couplings (e.g., electro-hydraulic wet connect, dry connect, inductive coupler, and the like), control lines (e.g., electrical, fiber optic, hydraulic, and the like), surveillance lines, drill bits and reamers, sensors or distributed sensors, downhole heat exchangers, valves and corresponding actuation devices, tool seals, packers, cement plugs, bridge plugs, and other wellbore isolation devices or components, and the like. Any of these components can be included in the systems and apparatuses generally described above and depicted in FIG. 2.

Composition for Treatment of a Subterranean Formation.

Various embodiments provide a composition for treatment of a subterranean formation. The composition can be any suitable composition that can be used to perform an embodiment of the method for treatment of a subterranean formation described herein.

For example, the composition can include a clay or shale stabilizer including at least one of a substituted guanidine group and a substituted guanidinium group. The composition can be or can include a downhole fluid, such as a drilling fluid, a fracturing fluid, a cementing fluid, a completion fluid, a logging fluid, a spotting fluid, or a packer fluid. The clay or shale stabilizer can have the following structure:

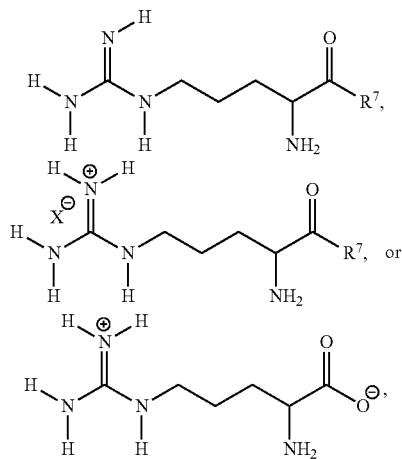

The variable $R^7$ can be selected from the group consisting of —OH, —OR$^8$, —O$^-$Y$^+$, and —O$^-$. The variable $R^8$ can be a ($C_1$-$C_{50}$)hydrocarbyl. The variable Y$^+$ is a counterion. The clay or shale stabilizer can be about 0.001 wt % to about 10 wt % of the composition.

Method for Preparing a Composition for Treatment of a Subterranean Formation.

In various embodiments, the present invention provides a method for preparing a composition for treatment of a subterranean formation. The method can be any suitable method that produces a composition described herein. For example, the method can include forming a composition including a clay or shale stabilizer including at least one of a substituted guanidine group and a substituted guanidinium group.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a method of treating a subterranean formation, the method comprising:
  placing a composition comprising a clay or shale stabilizer comprising at least one of a substituted guanidine group and a substituted guanidinium group in a subterranean formation.

Embodiment 2 provides the method of Embodiment 1, wherein the method further comprises obtaining or providing the composition, wherein the obtaining or providing of the composition occurs above-surface.

Embodiment 3 provides the method of any one of Embodiments 1-2, wherein the method further comprises obtaining or providing the composition, wherein the obtaining or providing of the composition occurs in the subterranean formation.

Embodiment 4 provides the method of any one of Embodiments 1-3, wherein the composition is at least one of a drilling fluid, fracturing fluid, cementing fluid, completion fluid, logging fluid, spotting fluid, and a packer fluid, or wherein the composition comprises at least one of a drilling fluid, fracturing fluid, cementing fluid, completion fluid, logging fluid, spotting fluid, and a packer fluid.

Embodiment 5 provides the method of any one of Embodiments 1-4, wherein the composition is oil- or water-based.

Embodiment 6 provides the method of any one of Embodiments 1-5, wherein the composition is a water- or oil-based emulsion.

Embodiment 7 provides the method of Embodiment 6, wherein the clay stabilizer is at least partially dissolved in the water- or oil-phase of the emulsion.

Embodiment 8 provides the method of any one of Embodiments 1-7, wherein the composition comprises a carrier fluid.

Embodiment 9 provides the method of Embodiment 8, wherein the carrier fluid is about 0.001 wt % to about 99.999 wt % of the composition.

Embodiment 10 provides the method of any one of Embodiments 8-9, wherein the carrier fluid is about 50 wt % to about 99.999 wt % of the composition.

Embodiment 11 provides the method of any one of Embodiments 1-10, wherein about 0.000.1 wt % to about 99.999 wt % of the composition is the clay or shale stabilizer.

Embodiment 12 provides the method of any one of Embodiments 1-11, wherein about 0.001 wt % to about 10 wt % of the composition is the clay or shale stabilizer.

Embodiment 13 provides the method of any one of Embodiments 1-12, wherein the clay or shale stabilizer has the structure:

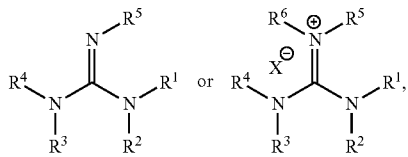

wherein
R$^1$, R$^2$, R$^3$, R$^4$, R$^5$, and R$^6$ are each independently selected from —H, halogen, an organic group, and substituted or unsubstituted (C$_1$-C$_{30}$)hydrocarbyl interrupted by 0, 1, 2, or 3 of at least one of —O—, —S—, and substituted or unsubstituted —NH—, or at least one pair of R$^1$, R$^2$, R$^3$, R$^4$, R$^5$, and R$^6$ together form a substituted or unsubstituted (C$_2$-C$_{20}$) hydrocarbylene such that at least two of the nitrogen atoms in the clay or shale stabilizer are part of a heterocycle including the substituted or unsubstituted (C$_2$-C$_{20}$)hydrocarbylene, wherein optionally at least one of R$^1$, R$^2$, R$^3$, R$^4$, R$^5$, and R$^6$ is bonded to at least one R$^1$, R$^2$, R$^3$, R$^4$, R$^5$, and R$^6$ on a different guanidine or guanidinium group in the same clay or shale stabilizer,
at least one of R$^1$, R$^2$, R$^3$, R$^4$, and R$^5$ is not —H, and X$^-$ is a counterion.

Embodiment 14 provides the method of Embodiment 13, wherein the clay or shale stabilizer has the structure:

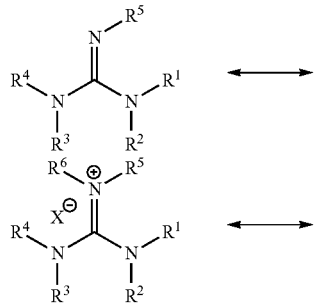 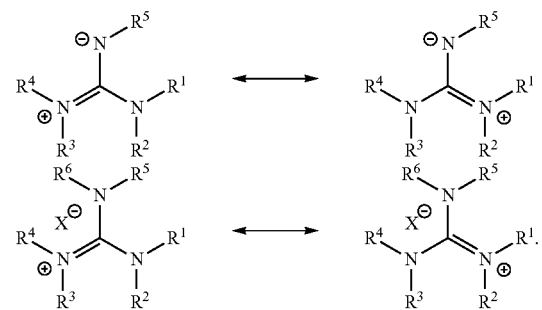

Embodiment 15 provides the method of any one of Embodiments 13-14, wherein R$^6$ is H.

Embodiment 16 provides the method of any one of Embodiments 13-15, wherein X$^-$ is selected from the group consisting of fluoro, chloro, iodo, bromo, nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate, acetate, formate, oxide, sulfide, nitride, arsenate, phosphate, arsenite, hydrogen phosphate, sulfate, thiosulfate, sulfite, carbonate, chromate, dichromate, peroxide, and oxalate.

Embodiment 17 provides the method of any one of Embodiments 13-16, wherein R$^2$, R$^3$, R$^4$, R$^5$, and R$^6$ are each independently selected from —H and substituted or unsubstituted (C$_1$-C$_{15}$)alkyl.

Embodiment 18 provides the method of any one of Embodiments 13-17, wherein R$^2$, R$^3$, R$^4$, R$^5$, and R$^6$ are each independently selected from —H and substituted or unsubstituted (C$_1$-C$_5$)alkyl.

Embodiment 19 provides the method of any one of Embodiments 13-18, wherein R$^2$, R$^3$, R$^4$, R$^5$, and R$^6$ are each —H.

Embodiment 20 provides the method of any one of Embodiments 13-19, wherein at least one pair of R$^1$, R$^2$, R$^3$, R$^4$, R$^5$, and R$^6$ together form a (C$_2$-C$_5$)alkylene such that at least two of the nitrogen atoms in the clay or shale stabilizer are part of a heterocycle including the (C$_2$-C$_5$)alkylene.

Embodiment 21 provides the method of any one of Embodiments 13-20, wherein at least one pair of R$^1$, R$^2$, R$^3$, R$^4$, R$^5$, and R$^6$ together form a (C$_3$)alkylene such that at least two of the nitrogen atoms in the clay or shale stabilizer are part of a heterocycle including the (C$_3$)alkylene.

Embodiment 22 provides the method of any one of Embodiments 13-21, wherein the clay or shale stabilizer is 1,5,7-triazabicyclo[4.4.0]dec-5-ene, having the structure:

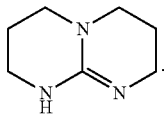

Embodiment 23 provides the method of any one of Embodiments 13-22, wherein the clay or shale stabilizer is a polymer.

Embodiment 24 provides the method of Embodiment 23, wherein the substituted guanidine group or substituted guanidinium group are pendant groups on the polymer.

Embodiment 25 provides the method of any one of Embodiments 23-24, wherein at least one of $R^1$, $R^2$, $R^3$, $R^4$, $R^5$, and $R^6$ is bonded to at least one $R^1$, $R^2$, $R^3$, $R^4$, $R^5$, and $R^6$ on a different guanidine or guanidinium group in the same clay or shale stabilizer.

Embodiment 26 provides the method of any one of Embodiments 1-25, wherein the clay or shale stabilizer comprises two or more of the guanidine or guanidinium groups connected to one another via a $(C_1-C_{30})$hydrocarbyl linker.

Embodiment 27 provides the method of any one of Embodiments 13-26, wherein the clay or shale stabilizer has the structure:

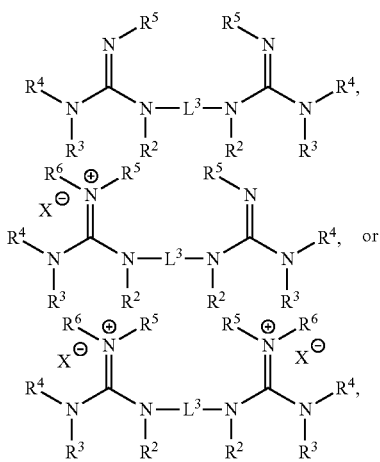

wherein
$R^2$, $R^3$, $R^4$, $R^5$, and $R^6$ are each independently selected from —H, halogen, an organic group, and substituted or unsubstituted $(C_1-C_{30})$hydrocarbyl interrupted by 0, 1, 2, or 3 of at least one of —O—, —S—, and substituted or unsubstituted —NH—, or at least one pair of $R^2$, $R^3$, $R^4$, $R^5$, and $R^6$ together form a substituted or unsubstituted $(C_2-C_{20})$hydrocarbylene such that at least two of the nitrogen atoms in the clay or shale stabilizer are part of a heterocycle including the substituted or unsubstituted $(C_2-C_{20})$ hydrocarbylene, wherein optionally at least one of $R^2$, $R^3$, $R^4$, $R^5$, and $R^6$ is bonded to at least one $R^2$, $R^3$, $R^4$, $R^5$, and $R^6$ on a different guanidine or guanidinium group in the same clay or shale stabilizer, $L^3$ is a substituted or unsubstituted $(C_1-C_{30})$hydrocarbyl interrupted by 0, 1, 2, or 3 of at least one of —O—, —S—, and substituted or unsubstituted —NH—, and
$X^-$ is a counterion.

Embodiment 28 provides the method of Embodiment 27, wherein $L^3$ is $(C_2-C_{20})$alkyl.

Embodiment 29 provides the method of any one of Embodiments 27-28, wherein the clay or shale stabilizer is 1,6-hexamethylene-bis-guanidine or 1,6-hexamethylene-bis-cyanoguanidine.

Embodiment 30 provides the method of any one of Embodiments 13-29, wherein $R^1$ is $-L^1-C(O)R^7$, $L^1$ is selected from the group consisting of a bond, a substituted or unsubstituted $(C_1-C_{30})$hydrocarbylene interrupted by 0, 1, 2, or 3 of at least one of —O—, —S—, and substituted or unsubstituted —NH—, wherein $L^1$ optionally comprises a bond to at least one $R^1$, $R^2$, $R^3$, $R^4$, $R^5$, and $R^6$ on a different guanidine or guanidinium group in the same clay or shale stabilizer,
$R^7$ is selected from the group consisting of —OH, —$OR^8$, —O—$Y^+$, —O—, and a bond to at least one $R^1$, $R^2$, $R^3$, $R^4$, $R^5$, and $R^6$ on a different guanidine or guanidinium group in the same clay or shale stabilizer,
$R^8$ is a substituted or unsubstituted $(C_1-C_{50})$hydrocarbyl interrupted by 0, 1, 2, or 3 of at least one of —O—, —S—, and substituted or unsubstituted —NH—, and
$Y^+$ is a counterion.

Embodiment 31 provides the method of Embodiment 30, wherein $L^1$ is a $(C_1-C_{30})$hydrocarbylene interrupted by 0, 1, 2, or 3 of at least one of —O—, —S—, and substituted or unsubstituted —NH—, and comprising at least one —$NH_2$ substituent.

Embodiment 32 provides the method of any one of Embodiments 30-31, wherein $L^1$ is a $(C_1-C_{15})$alkylene comprising at least one —$NH_2$ substituent.

Embodiment 33 provides the method of any one of Embodiments 30-32, wherein $L^1$ is a butylene comprising at least one —$NH_2$ substituent.

Embodiment 34 provides the method of Embodiment 33, wherein $L^1$ is —$(CH_2)_3$—$CH(NH_2)$—.

Embodiment 35 provides the method of any one of Embodiments 30-34, wherein $R^8$ is a $(C_1-C_{50})$alkyl.

Embodiment 36 provides the method of any one of Embodiments 30-35, wherein $R^8$ is a $(C_1-C_{15})$alkyl.

Embodiment 37 provides the method of any one of Embodiments 30-36, wherein $R^8$ is a $(C_1-C_5)$alkyl.

Embodiment 38 provides the method of any one of Embodiments 30-37, wherein $R^8$ is ethyl.

Embodiment 39 provides the method of any one of Embodiments 30-38, wherein $Y^+$ is selected from the group consisting of $Na^+$, $K^+$, $Li^+$, $H^+$, $NH_4$, $Ca^{2+}$, $Mg^{2+}$, $Zn^{2+}$, and $Al^{3+}$.

Embodiment 40 provides the method of any one of Embodiments 30-39, wherein the clay or shale stabilizer has the structure:

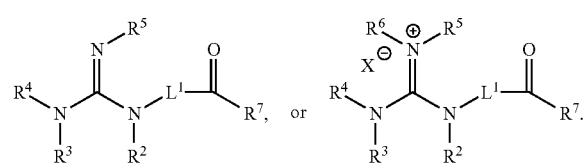

Embodiment 41 provides the method of any one of Embodiments 30-40, wherein the clay or shale stabilizer is a polymer comprising repeating units having the structure:

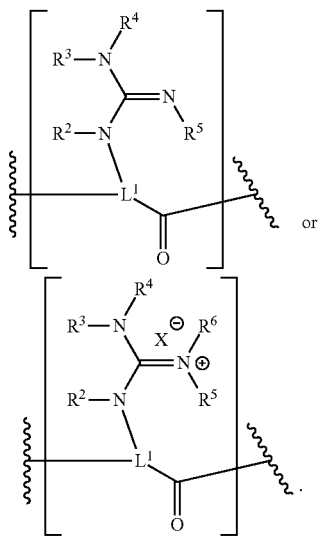

or

Embodiment 42 provides the method of any one of Embodiments 30-41, wherein the clay or shale stabilizer has the structure:

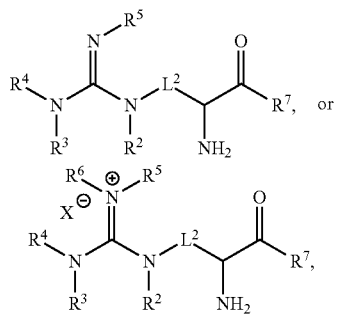

wherein

L² is selected from the group consisting of a bond and a substituted or unsubstituted $(C_1-C_{28})$hydrocarbylene interrupted by 0, 1, 2, or 3 of at least one of —O—, —S—, and substituted or unsubstituted —NH—.

Embodiment 43 provides the method of any one of Embodiments 30-42, wherein the clay or shale stabilizer is a polymer comprising repeating units having the structure:

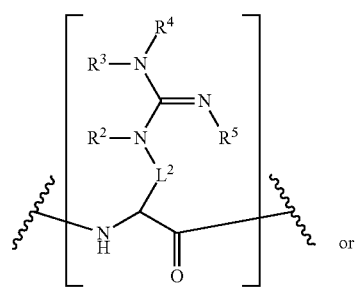

or

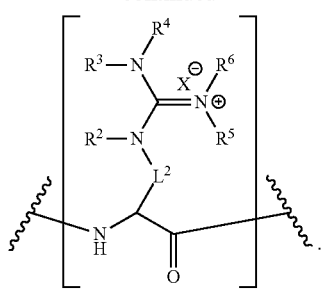

Embodiment 44 provides the method of any one of Embodiments 42-43, wherein L² is a $(C_1-C_{15})$alkylene.

Embodiment 45 provides the method of any one of Embodiments 42-44, wherein L² is propylene.

Embodiment 46 provides the method of any one of Embodiments 42-45, wherein L² is —(CH₂)₃—.

Embodiment 47 provides the method of any one of Embodiments 13-46, wherein the clay or shale stabilizer has the structure:

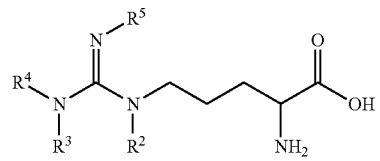

or a salt thereof,

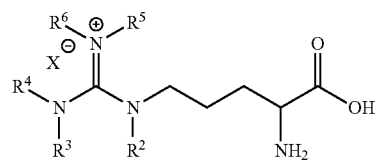

or a salt thereof, or

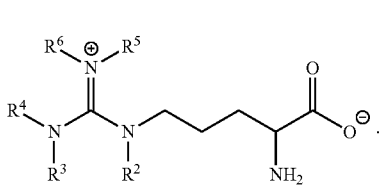

Embodiment 48 provides the method of any one of Embodiments 13-47, wherein the clay or shale stabilizer is a polymer comprising repeating units having the structure:

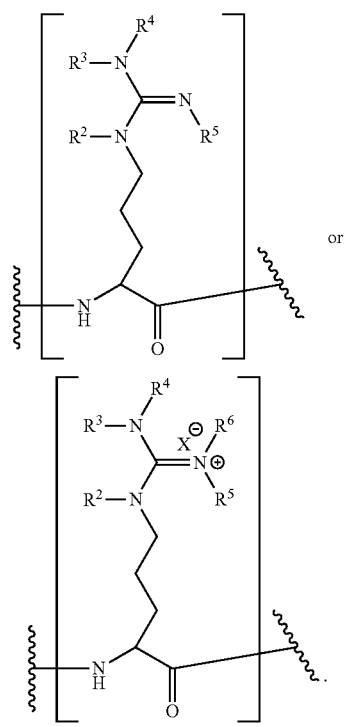

Embodiment 49 provides the method of any one of Embodiments 1-48, wherein the clay or shale stabilizer has the structure:

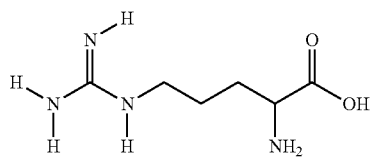

or a salt thereof,

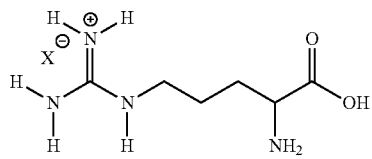

or a salt thereof, or

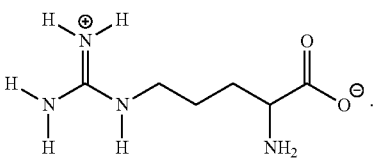 [SMILES: NC(=[NH2+])NCCCC(N)C(=O)[O-]]

Embodiment 50 provides the method of any one of Embodiments 1-49, wherein the clay or shale stabilizer is a polymer comprising repeating units having the structure:

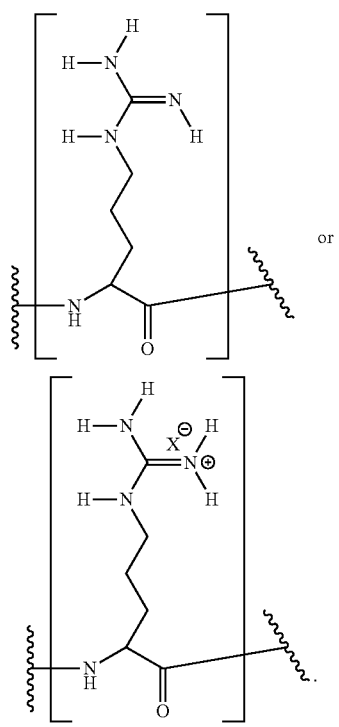

Embodiment 51 provides the method of any one of Embodiments 1-50, wherein the clay or shale stabilizer has the structure:

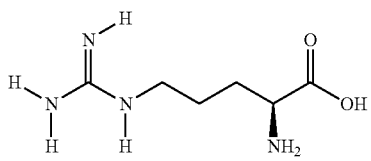 [SMILES: [H]/N=C(/N)NCCC[C@H](N)C(=O)O]

or a salt thereof,

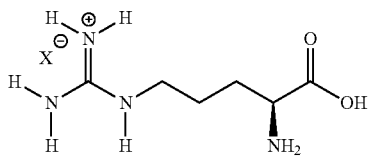

or a salt thereof,

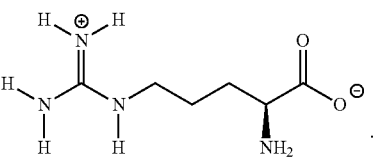 [SMILES: NC(=[NH2+])NCCC[C@H](N)C(=O)[O-]]

Embodiment 52 provides the method of any one of Embodiments 1-51, wherein the clay or shale stabilizer is a polymer comprising repeating units having the structure:

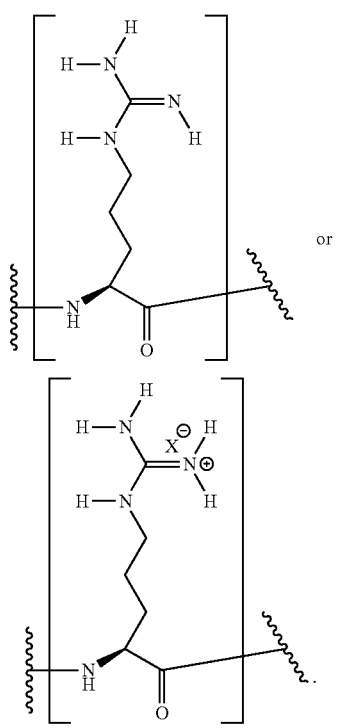

Embodiment 53 provides the method of any one of Embodiments 30-52, wherein the clay or shale stabilizer has the structure:

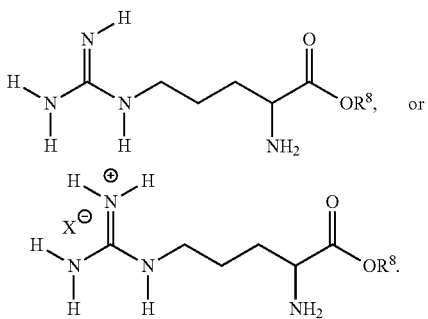

Embodiment 54 provides the method of Embodiment 53, wherein $R^8$ is $(C_1-C_5)$alkyl.

Embodiment 55 provides the method of any one of Embodiments 53-54, wherein $R^8$ is ethyl.

Embodiment 56 provides the method of any one of Embodiments 30-55, wherein the clay or shale stabilizer has the structure:

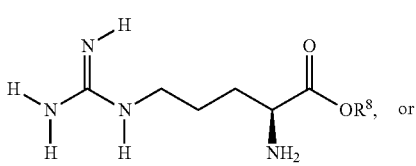

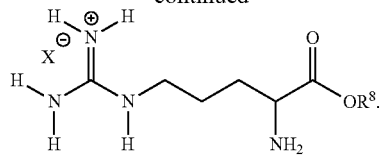

Embodiment 57 provides the method of Embodiment 56, wherein $R^8$ is $(C_1-C_5)$alkyl.

Embodiment 58 provides the method of any one of Embodiments 56-57, wherein $R^8$ is ethyl.

Embodiment 59 provides the method of any one of Embodiments 1-58, wherein the composition comprises one or more second clay or shale stabilizers.

Embodiment 60 provides the method of Embodiment 59, wherein the second clay or shale stabilizer is at least one of a substituted or unsubstituted amine, potassium chloride, a crosslinked polyvinylpyrrolidone, an inorganic phosphate, a polyalkoxy diamine or a salt thereof, choline or a choline derivative, an oligomethylene diamine or a salt thereof, an addition product of carboxymethyl cellulose and an organic amine, 1,2-cyclohexanediamine or a salt thereof, a salt of a phosphoric acid ester of an oxyalkylated polyol, a combination of a partially hydrolyzed acrylic copolymer potassium chloride and polyanionic cellulose, a quaternary ammonium compound, a polymer based on dialkyl aminoalkyl methacrylate, an aqueous solution containing a polymer with hydrophilic and hydrophobic groups, and a reaction product of a polyhydroxyalkane and an alkylene oxide.

Embodiment 61 provides the method of any one of Embodiments 1-60, wherein the composition further comprises a viscosifier.

Embodiment 62 provides the method of Embodiment 61, wherein the viscosifier is crosslinked or uncrosslinked.

Embodiment 63 provides the method of any one of Embodiments 61-62, wherein the viscosifier comprises at least one of a linear polysaccharide, and a polymer of a $(C_2-C_{50})$hydrocarbyl having at least one carbon-carbon unsaturated aliphatic bond therein, wherein the $(C_2-C_{50})$ hydrocarbyl is substituted or unsubstituted.

Embodiment 64 provides the method of any one of Embodiments 1-63, wherein the composition further comprises a crosslinker.

Embodiment 65 provides the method of Embodiment 64, wherein the crosslinker comprises at least one of chromium, aluminum, antimony, zirconium, titanium, calcium, boron, iron, silicon, copper, zinc, magnesium, and an ion thereof.

Embodiment 66 provides the method of any one of Embodiments 64-65, wherein the crosslinker comprises at least one of boric acid, borax, a borate, a $(C_1-C_{30})$hydrocarbylboronic acid, a $(C_1-C_{30})$hydrocarbyl ester of a $(C_1-C_{30})$hydrocarbylboronic acid, a $(C_1-C_{30})$hydrocarbylboronic acid-modified polyacrylamide, ferric chloride, disodium octaborate tetrahydrate, sodium metaborate, sodium diborate, sodium tetraborate, disodium tetraborate, a pentaborate, ulexite, colemanite, magnesium oxide, zirconium lactate, zirconium triethanol amine, zirconium lactate triethanolamine, zirconium carbonate, zirconium acetylacetonate, zirconium malate, zirconium citrate, zirconium diisopropylamine lactate, zirconium glycolate, zirconium triethanol amine glycolate, zirconium lactate glycolate, titanium lactate, titanium malate, titanium citrate, titanium ammonium lactate, titanium triethanolamine, titanium acetylacetonate, aluminum lactate, and aluminum citrate.

Embodiment 67 provides the method of any one of Embodiments 64-66, wherein the crosslinker comprises at least one of a $(C_1-C_{20})$alkylenebiacrylamide, a poly$((C_1-C_{20})$alkenyl)-substituted mono- or poly-$(C_1-C_{20})$alkyl ether, a poly$(C_2-C_{20})$alkenylbenzene, alkyl diacrylate, ethylene glycol diacrylate, ethylene glycol dimethacrylate, polyethylene glycol diacrylate, polyethylene glycol dimethacrylate, ethoxylated bisphenol A diacrylate, ethoxylated bisphenol A dimethacrylate, ethoxylated trimethylol propane triacrylate, ethoxylated trimethylol propane trimethacrylate, ethoxylated glyceryl triacrylate, ethoxylated glyceryl trimethacrylate, ethoxylated pentaerythritol tetraacrylate, ethoxylated pentaerythritol tetramethacrylate, ethoxylated dipentaerythritol hexaacrylate, polyglyceryl monoethylene oxide polyacrylate, polyglyceryl polyethylene glycol polyacrylate, dipentaerythritol hexaacrylate, dipentaerythritol hexamethacrylate, neopentyl glycol diacrylate, neopentyl glycol dimethacrylate, pentaerythritol triacrylate, pentaerythritol trimethacrylate, trimethylol propane triacrylate, trimethylol propane trimethacrylate, tricyclodecane dimethanol diacrylate, tricyclodecane dimethanol dimethacrylate, 1,6-hexanediol diacrylate, and 1,6-hexanediol dimethacrylate.

Embodiment 68 provides the method of any one of Embodiments 1-67, further comprising combining the composition with an aqueous or oil-based fluid comprising a drilling fluid, stimulation fluid, fracturing fluid, spotting fluid, clean-up fluid, completion fluid, remedial treatment fluid, abandonment fluid, pill, acidizing fluid, cementing fluid, packer fluid, logging fluid, or a combination thereof, to form a mixture, wherein the placing the composition in the subterranean formation comprises placing the mixture in the subterranean formation.

Embodiment 69 provides the method of Embodiment 68, wherein the cementing fluid comprises Portland cement, pozzolana cement, gypsum cement, high alumina content cement, slag cement, silica cement, or a combination thereof.

Embodiment 70 provides the method of any one of Embodiments 1-69, wherein at least one of prior to, during, and after the placing of the composition in the subterranean formation, the composition is used in the subterranean formation, at least one of alone and in combination with other materials, as a drilling fluid, stimulation fluid, fracturing fluid, spotting fluid, clean-up fluid, completion fluid, remedial treatment fluid, abandonment fluid, pill, acidizing fluid, cementing fluid, packer fluid, logging fluid, or a combination thereof.

Embodiment 71 provides the method of any one of Embodiments 1-70, wherein the composition further comprises water, saline, aqueous base, oil, organic solvent, synthetic fluid oil phase, aqueous solution, alcohol or polyol, cellulose, starch, alkalinity control agent, acidity control agent, density control agent, density modifier, emulsifier, dispersant, polymeric stabilizer, crosslinking agent, polyacrylamide, polymer or combination of polymers, antioxidant, heat stabilizer, foam control agent, solvent, diluent, plasticizer, filler or inorganic particle, pigment, dye, precipitating agent, rheology modifier, oil-wetting agent, set retarding additive, surfactant, corrosion inhibitor, gas, weight reducing additive, heavy-weight additive, lost circulation material, filtration control additive, salt, fiber, thixotropic additive, breaker, crosslinker, gas, rheology modifier, curing accelerator, curing retarder, pH modifier, chelating agent, scale inhibitor, enzyme, resin, water control material, polymer, oxidizer, a marker, Portland cement, pozzolana cement, gypsum cement, high alumina content cement, slag cement, silica cement, fly ash, metakaolin, shale, zeolite, a crystalline silica compound, amorphous silica, fibers, a hydratable clay, microspheres, pozzolan lime, or a combination thereof.

Embodiment 72 provides the method of any one of Embodiments 1-71, wherein the placing of the composition in the subterranean formation comprises fracturing at least part of the subterranean formation to form at least one subterranean fracture.

Embodiment 73 provides the method of any one of Embodiments 1-72, wherein the composition further comprises a proppant, a resin-coated proppant, or a combination thereof.

Embodiment 74 provides the method of any one of Embodiments 1-73, wherein the placing of the composition in the subterranean formation comprises pumping the composition through a drill string disposed in a wellbore, through a drill bit at a downhole end of the drill string, and back above-surface through an annulus.

Embodiment 75 provides the method of Embodiment 74, further comprising processing the composition exiting the annulus with at least one fluid processing unit to generate a cleaned composition and recirculating the cleaned composition through the wellbore.

Embodiment 76 provides a system for performing the method of any one of Embodiments 1-75, the system comprising:
a tubular disposed in the subterranean formation; and
a pump configured to pump the composition in the subterranean formation through the tubular.

Embodiment 77 provides a system for performing the method of any one of Embodiments 1-75, the system comprising:
a drillstring disposed in a wellbore, the drillstring comprising a drill bit at a downhole end of the drillstring;
an annulus between the drillstring and the wellbore; and
a pump configured to circulate the composition through the drill string, through the drill bit, and back above-surface through the annulus.

Embodiment 78 provides a method of treating a subterranean formation, the method comprising:
placing in a subterranean formation a drilling fluid, fracturing fluid, cementing fluid, completion fluid, logging fluid, spotting fluid, or a packer fluid comprising a clay or shale stabilizer having the following structure

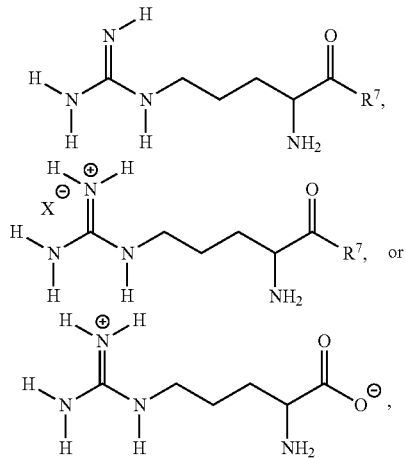

wherein
$R^7$ is selected from the group consisting of —OH, —OR$^8$, —[O]Y$^+$, and —O$^-$, R[8] is a $(C_1-C_{50})$hydrocarbyl,
Y[+] is a counterion, and
the clay or shale stabilizer is about 0.001 wt % to about 10 wt % of the drilling fluid, fracturing fluid, or cementing fluid.

Embodiment 79 provides a method of treating a subterranean formation, the method comprising:
placing a composition comprising a clay or shale stabilizer in a subterranean formation, the clay or shale stabilizer comprising at least one of an unsubstituted guanidine and an unsubstituted guanidinium, wherein the guanidine and guanidinium are free of complexation with polyvalent metals.

Embodiment 80 provides the method of Embodiment 79, wherein the guanidine and guanidinium are free of complexation with metals.

Embodiment 81 provides a system comprising:
a composition comprising a clay or shale stabilizer comprising at least one of a substituted guanidine group and a substituted guanidinium group; and
a subterranean formation comprising the composition therein.

Embodiment 82 provides the system of Embodiment 81, further comprising
a drillstring disposed in a wellbore, the drillstring comprising a drill bit at a downhole end of the drillstring;
an annulus between the drillstring and the wellbore; and
a pump configured to circulate the composition through the drill string, through the drill bit, and back above-surface through the annulus.

Embodiment 83 provides the system of Embodiment 82, further comprising a fluid processing unit configured to process the composition exiting the annulus to generate a cleaned drilling fluid for recirculation through the wellbore.

Embodiment 84 provides the system of any one of Embodiments 81-83, further comprising
a tubular disposed in the subterranean formation; and
a pump configured to pump the composition in the subterranean formation through the tubular.

Embodiment 85 provides a composition for treatment of a subterranean formation, the composition comprising:
a clay or shale stabilizer comprising at least one of a substituted guanidine group and a substituted guanidinium group.

Embodiment 86 provides the composition of Embodiment 85, wherein the composition is at least one of a drilling fluid, fracturing fluid, cementing fluid, completion fluid, logging fluid, spotting fluid, and a packer fluid.

Embodiment 87 provides a drilling fluid, fracturing fluid, cementing fluid, completion fluid, logging fluid, spotting fluid, or a packer fluid for treatment of a subterranean formation, the composition comprising:
a clay or shale stabilizer having the following structure

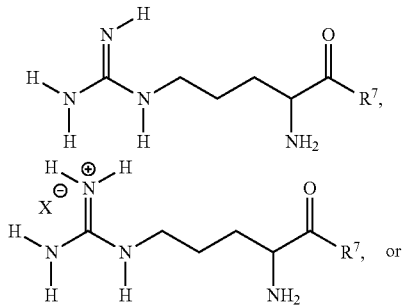

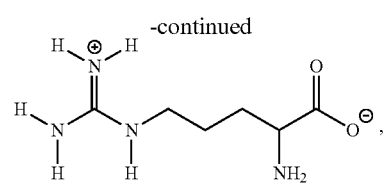

wherein
R[7] is selected from the group consisting of —OH, —OR[8], —[O[−]]Y[+], and —O[−],
R[8] is a $(C_1-C_{50})$hydrocarbyl,
Y[+] is a counterion, and
the clay or shale stabilizer is about 0.001 wt % to about 10 wt % of the drilling fluid, fracturing fluid, cementing fluid, completion fluid, logging fluid, spotting fluid, or the packer fluid.

Embodiment 88 provides a method of preparing a composition for treatment of a subterranean formation, the method comprising:
forming a composition comprising
a clay or shale stabilizer comprising at least one of a substituted guanidine group and a substituted guanidinium group.

Embodiment 88 provides the composition, method, or system of any one or any combination of Embodiments 1-87 optionally configured such that all elements or options recited are available to use or select from.

What is claimed is:
1. A system comprising:
a tubular disposed in a subterranean formation;
a composition comprising a clay or shale stabilizer comprising at least one of the following structures:

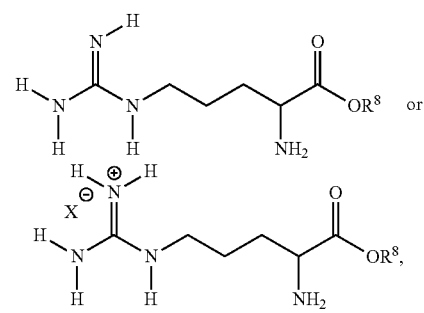

wherein the variable R[8] is a $(C_2-C_5)$ alkyl group; and
a pump configured to pump the composition in the subterranean formation through the tubular.

2. The system of claim 1 further comprising:
a drillstring disposed in a wellbore, the drillstring comprising a drill bit at a downhole end of the drillstring;
an annulus between the drillstring and the wellbore; and
a pump configured to circulate the composition through the drill string, through the drill bit, and back above-surface through the annulus.

3. The system of claim 1, wherein the system is configured for delivering the composition for at least one of a drilling operation, fracturing operation, cementing operation, completion operation, logging operation, spotting operation, and a packer operation.

4. The system of claim 1, wherein the composition is oil- or water-based or wherein the composition is a water- or oil-based emulsion.

5. The system of claim 1, wherein the clay or shale stabilizer further comprises at least one of the following structures:

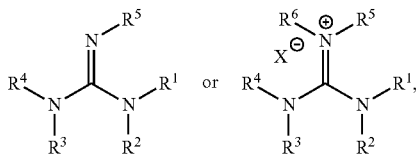

wherein
$R^1$, $R^2$, $R^3$, $R^4$, $R^5$, and $R^6$ are each independently selected from —H, halogen, an organic group, and substituted or unsubstituted ($C_1$-$C_{30}$)hydrocarbyl interrupted by 0, 1, 2, or 3 of at least one of —O—, —S—, and substituted or unsubstituted —NH—, or at least one pair of $R^1$, $R^2$, $R^3$, $R^4$, $R^5$, and $R^6$ together form a substituted or unsubstituted ($C_2$-$C_{20}$)hydrocarbylene such that at least two of the nitrogen atoms in the clay or shale stabilizer are part of a heterocycle including the substituted or unsubstituted ($C_2$-$C_{20}$)hydrocarbylene, wherein optionally at least one of $R^1$, $R^2$, $R^3$, $R^4$, $R^5$, and $R^6$ is bonded to at least one $R^1$, $R^2$, $R^3$, $R^4$, $R^5$, and $R^6$ on a different guanidine or guanidinium group in the same clay or shale stabilizer, at least one of $R^1$, $R^2$, $R^3$, $R^4$, and $R^5$ is not —H, and $X^-$ is a counterion.

6. The system of claim 5, wherein $X^-$ is selected from the group consisting of fluoro, chloro, iodo, bromo, nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate, acetate, formate, oxide, sulfide, nitride, arsenate, phosphate, arsenite, hydrogen phosphate, sulfate, thiosulfate, sulfite, carbonate, chromate, dichromate, peroxide, and oxalate.

7. The system of claim 1, wherein the clay or shale stabilizer further comprises 1,5,7-triazabicyclo[4.4.0]dec-5-ene, having the structure:

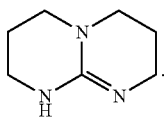

8. The system of claim 1, wherein the clay or shale stabilizer further comprises:

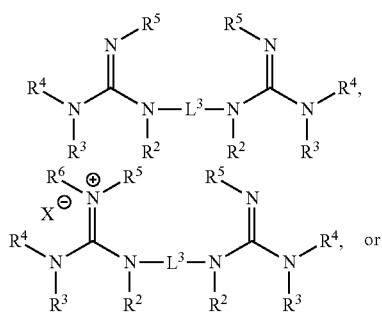

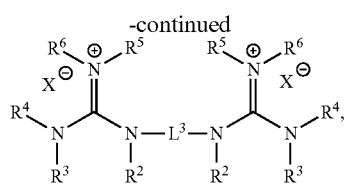

wherein
$R^2$, $R^3$, $R^4$, $R^5$, and $R^6$ are each independently selected from —H, halogen, an organic group, and substituted or unsubstituted ($C_1$-$C_{30}$)hydrocarbyl interrupted by 0, 1, 2, or 3 of at least one of —O—, —S—, and substituted or unsubstituted —NH—, or at least one pair of $R^2$, $R^3$, $R^4$, $R^5$, and $R^6$ together form a substituted or unsubstituted ($C_2$-$C_{20}$)hydrocarbylene such that at least two of the nitrogen atoms in the clay or shale stabilizer are part of a heterocycle including the substituted or unsubstituted ($C_2$-$C_{20}$) hydrocarbylene, wherein optionally at least one of $R^2$, $R^3$, $R^4$, $R^5$, and $R^6$ is bonded to at least one $R^2$, $R^3$, $R^4$, $R^5$, and $R^6$ on a different guanidine or guanidinium group in the same clay or shale stabilizer,
$L^3$ is a substituted or unsubstituted ($C_1$-$C_{30}$)hydrocarbyl interrupted by 0, 1, 2, or 3 of at least one of —O—, —S—, and substituted or unsubstituted —NH—, and
$X^-$ is a counterion.

9. The system of claim 8, wherein $L^3$ is ($C_2$-$C_{20}$)alkyl.

10. The system of claim 8, wherein
$R^1$ is -$L^1$-C(O)$R^7$,
$L^1$ is selected from the group consisting of a bond, a substituted or unsubstituted ($C_1$-$C_{30}$)hydrocarbylene interrupted by 0, 1, 2, or 3 of at least one of —O—, —S—, and substituted or unsubstituted —NH—, wherein $L^1$ optionally comprises a bond to at least one $R^1$, $R^2$, $R^3$, $R^4$, $R^5$, and $R^6$ on a different guanidine or guanidinium group in the same clay or shale stabilizer,
$R^7$ is selected from the group consisting of —OH, —$OR^8$, —$O^-Y^+$, —$O^-$, and a bond to at least one $R^1$, $R^2$, $R^3$, $R^4$, $R^5$, and $R^6$ on a different guanidine or guanidinium group in the same clay or shale stabilizer,
$R^8$ is a substituted or unsubstituted ($C_1$-$C_{50}$)hydrocarbyl interrupted by 0, 1, 2, or 3 of at least one of —O—, —S—, and substituted or unsubstituted —NH—, and
$Y^+$ is a counterion.

11. The system of claim 10, wherein $Y^+$ is selected from the group consisting of $Na^+$, $K^+$, $Li^+$, $H^+$, $NH_4^+$, $Ca^{2+}$, $Mg^{2+}$, $Zn^{2+}$, and $Al^{3+}$.

12. The system of claim 1, wherein the clay or shale stabilizer further comprises 1,6-hexamethylene-bis-guanidine or 1,6-hexamethylene-bis-cyanoguanidine.

13. The system of claim 1, wherein the clay or shale stabilizer further comprises at least one of the following structures:

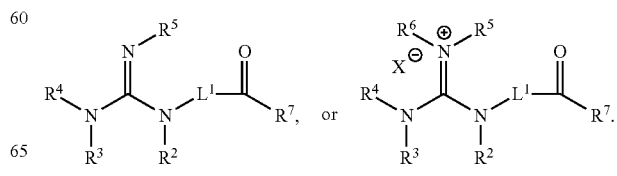

14. The system of claim 1, wherein the clay or shale stabilizer further comprises a polymer comprising repeating units having the structure:

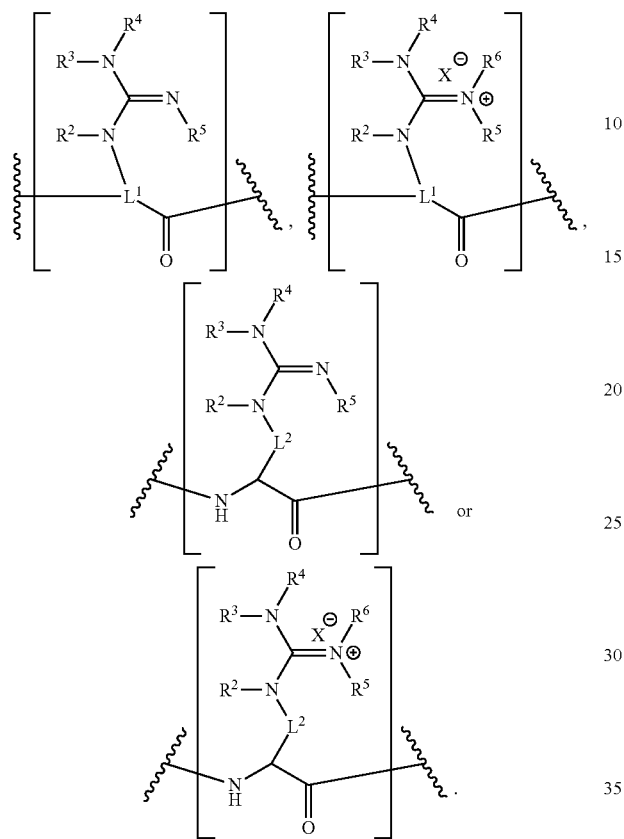

15. The system of claim 1, wherein the clay or shale stabilizer further comprises at least one of the following structures:

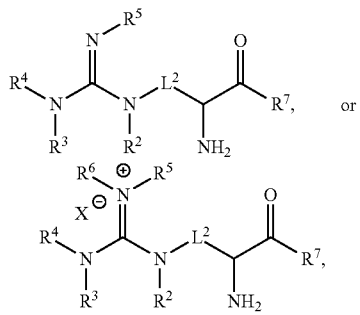

wherein
   $L^2$ is selected from the group consisting of a bond and a substituted or unsubstituted $(C_1\text{-}C_{28})$hydrocarbylene interrupted by 0, 1, 2, or 3 of at least one of —O—, —S—, and substituted or unsubstituted —NH—.

16. The system of claim 1, wherein the clay or shale stabilizer further comprises a polymer comprising repeating units having the structure:

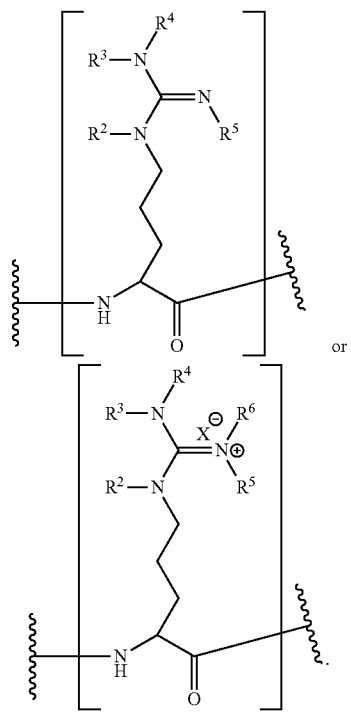

17. The system of claim 1 wherein clay or shale stabilizer is a substituted arginine with at least one of the following structures:

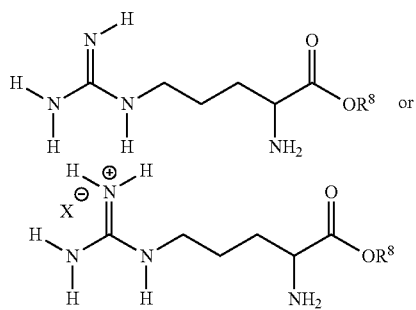

wherein the variable $R^8$ is ethyl.

18. A method of treating a subterranean formation, the method comprising:
   preparing a treatment fluid comprising:
      a base fluid, and a clay or shale stabilizer comprising:

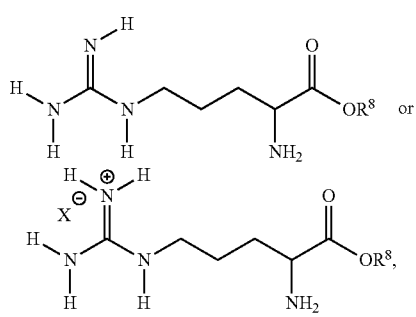

wherein the variable $R^8$ is a $(C_2-C_5)$ alkyl group, and at least one of:
- a. 1,5,7-triazabicyclo[4.4.0]dec-5-ene, having the structure:
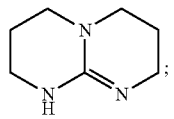
- b. 1,6-hexamethylene-bis-guanidine;
- c. 1,6-hexamethylene-bis-cyanoguanidine;
- d. arginine, substituted arginine, or any salt thereof; or
- e. polyarginine; and
placing the treatment fluid into a subterranean formation.
* * * * *